(12) United States Patent
Ibrahim et al.

(10) Patent No.: US 11,345,692 B1
(45) Date of Patent: May 31, 2022

(54) 3-VINYLQUINOLINES AS CANCER CELLS INHIBITORS

(71) Applicant: King Abdulaziz University, Jeddah (SA)

(72) Inventors: Tarek Salah Ibrahim, Jeddah (SA); Mohamed Moustafa Hawwas, Assuit (EG); Azizah M. Malebari, Jeddah (SA); Moustafa E. El-Araby, Jeddah (SA); Abdelsattar M. Omar, Jeddah (SA)

(73) Assignee: King Abdulaziz University, Jeddah (SA)

( * ) Notice: Subject to any disclaimer, the term of this patent is extended or adjusted under 35 U.S.C. 154(b) by 46 days.

(21) Appl. No.: 17/098,744

(22) Filed: Nov. 16, 2020

Related U.S. Application Data

(62) Division of application No. 16/924,761, filed on Jul. 9, 2020, now Pat. No. 10,882,852.

(51) Int. Cl.
*C07D 413/06* (2006.01)
*A61P 35/00* (2006.01)
*C07D 401/06* (2006.01)

(52) U.S. Cl.
CPC ............ *C07D 413/06* (2013.01); *A61P 35/00* (2018.01); *C07D 401/06* (2013.01)

(58) Field of Classification Search
CPC .................................................. C07D 413/06
USPC ......................................................... 514/314
See application file for complete search history.

(56) References Cited

U.S. PATENT DOCUMENTS 10,882,852 B1 * 1/2021 Ibrahim ............... C07D 413/06

\* cited by examiner

*Primary Examiner* — Nizal S Chandrakumar
(74) *Attorney, Agent, or Firm* — W & C IP

(57) ABSTRACT

3-vinylquinolines analogs and methods of synthesizing the derivatives/analogs are provided. In particular, the compounds are useful for the treatment of cancer.

10 Claims, 13 Drawing Sheets

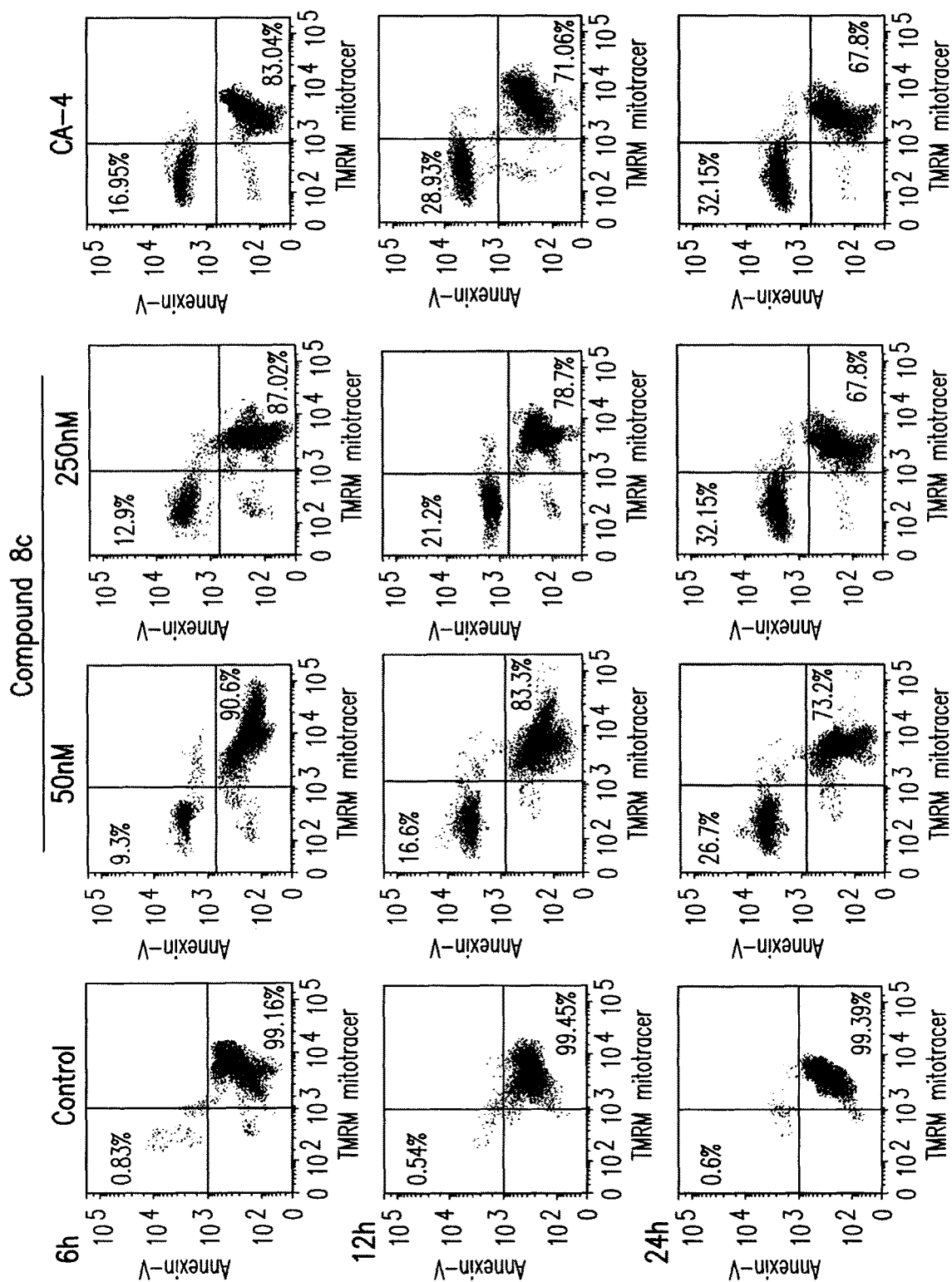

(B)

3-VINYLQUINOLINES AS CANCER CELLS INHIBITORS

FIELD OF THE INVENTION

The invention generally is related to small molecules with a 3-vinylquinoline core, with anticancer activities, their methods of synthesis, and the use of these molecules for the treatment of cancer. In particular, the small molecules disclosed herein are active against breast cancer, leukemia, colon cancer and cervical cancer.

BACKGROUND

Cancer is a group of diseases resulting from cellular changes, e.g., uncontrolled growth and division of abnormal cells, which lead to death of the afflicted subject. Recently, targeted anticancer therapy represents an important class of antineoplastic agents [1]. Pharmaceutical companies focus on selectivity of various therapies toward special cancer types [2]. This category of drugs interferes with, for example, specific enzymes, proteins, or blocking certain receptors, preventing cancer cell division and growth. Tubulin polymerization inhibitors are one of the most widely researched and represent potential examples for targeted cancer therapies [3]. Tubulin is a globular protein that plays a substantial role in cell mitosis. Microtubules (MTs) are basic constituents of eukaryotic cells, and are cytoskeletons constructed by the association of α- and β-tubulin heterodimers with a head and tail pattern to form hollow cylindrical tubes (nearly 25 nm in diameter) [4-7]. MTs play a crucial role in many fundamental cellular processes such as cell formation, motility, cell secretion, signalling, maintenance of cell shape, regulation of the intracellular transport and cell division [8-10]. Due to these multiple functions, the microtubule system has become an attractive and significant approach in cancer chemotherapy [11, 12].

Disruption of MTs or tubulin dynamics exposes the cell to mitotic arrest in the G2/M phase cell cycle and consequently induction of cellular apoptosis [13, 14].

Today, there are numerous natural products, identified as microtubule-interfering agents (MIAs), such as paclitaxel, vincristine, vinblastine and colchicine, that are in wide use. MIAs bind to tubulin at specific binding sites namely taxol, vinca and colchicine binding sites, through two different mechanisms of action, either the enhancement or inhibition of tubulin polymerization [15]. Indeed, both actions deteriorate the microtubule dynamics and prevent cell proliferation. Microtubule stabilizers (e.g. paclitaxel) stimulate microtubule polymerization through binding to the taxol binding site [16]. In turn, microtubule destabilizers such as vinca alkaloids (e.g. vinblastine and vincristine) and colchicine inhibit the polymerization of microtubules through binding to the vinca- and colchicine-domains, respectively [17].

Generally speaking, more attention has been focused on the inhibitors which bind to colchicine domains, due to their impact on the ABC-transporter-mediated drug resistance [18, 19]. Combretastatin A-4 has been reported as the most potent antimitotic agent of this family against several tumor cells [20]. It has vascular disrupting activity against the tumor cell vasculature and thus prevents blood supply to solid tumors resulting in apoptosis [3, 21, 22]. Phases II and III studies are underway to address the limitations of currently existing tubulin-targeted drugs [23, 24]. CA-4 was first isolated in 1989 from the bark of the South African willow tree *Combretum caffrum* [25]. Given the structural simplicity, significant activity, accompanied with issues of low aqueous solubility, CA-4 has been significantly studied as a lead pharmacophore for deciphering tubulin and MTs functions and properties. A structure activity relationship (SAR) profile conducted on CA-4 revealed three key features were required to show optimum cytotoxic activity. These includes: 3,4,5-trimethoxy moiety on ring A (essential for the activity), cis-orientation of both the aromatic rings i.e. trans-orientation is inactive, and the presence of small substituent on ring B e.g. methoxy group (important for the activity). Accordingly, we explored these elements for modification and optimization. CA-4 is vulnerable to undergo transformation to the inactive trans-form. In this respect, different studies investigated inhibiting cis-trans transformation of the double bond by inserting five membered heteroaromatic rings, as a favourable alteration for more restriction. Examples included oxadiazole, isoxazole and imidazole. These compounds showed more pronounced activity than CA-4 against cancer cell lines [26-28]. Further, from the point of view that a fused heterocyclic is of much greater interest than monocyclic, the quinoline nucleus has been tested as a bioisoster for ring B as another focus of study [29]. Fortunately, the later compound showed 10-fold potent anticancer properties in comparison to CA-4 with retained tubulin inhibition mechanism [30]. Despite the encouraging activity of both modifications, the synthesis of such analogues bearing both modes in one compact structure, with the favor of retention of the cisoid alkenyl bond i.e. more restriction has not been done prior to this invention. This could open the door to better understand binding mode of interaction with tubulin to magnify the potency and efficacy of the lead candidate.

SUMMARY

In making this invention, we aimed to optimize CA-4 through synthesis a series of novel CA-4 analogs, as potent tubulin inhibitors working through two modes. All the synthesized analogs in both modes were bearing the same ring A of CA-4 in the skeleton. Concerning mode one, the target compounds were synthesized through using 3,4,5-trimethoxyphenyl moiety (ring A) and quinolyl moiety (ring B) with variation of electronic substituents effects. On the other hand, in mode two, the compounds were designed to increase structure rigidity through direct introduction of a ring C (e.g., 1,3-oxazol-5-ones and 1,3-imidazol-4-ones) to the cis-olefinic bond which may create another type of desirable conformational and configurational restriction that could prevent in vivo isomerization of CA-4 analogs into the inactive trans-isomer. The molecular hybrid tactic, utilized in both modes, for our targeted analogs may improve the water solubility, lower the toxicity, and enhance the chemical stability of one or more lead candidates. The novel CA-4 analogs were screened for their antiproliferative activity in HL-60, MCF-7, HCT-116 and HeLa cancer cells, after which further mechanistic biochemical investigations were performed.

Based on our investigations, provided herein are compounds for the treatment of cancer, and methods of making the compounds. In particular, the compounds are quinoline derivatives which target cancer cells and which act as tubulin polymerization inhibitors. The compounds comprise a quinolyl moiety and phenyl moiety, such as a five membered ring. In some aspects, the compounds are 3-vinylquinoline derivatives.

Some embodiments of the invention relate to a compound having the general structural formula:

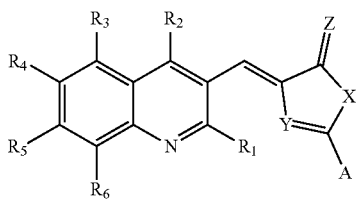

Formula I wherein,

R1 is $OC_nH_{2n+1}$ or $C_nH_{2n+1}$ group;

R2, R3, R4, R5 and R6 are the same of different and are independently substituted or unsubstituted alkyl, alkoxy, aryl, acyl, halogenated alkyl, halogenated alkoxy, hydroxylalkyl, O-aryl nitrile, halogen (F, Br, Cl, or I), or hydrogen;

X, Y and Z are the same or different and are independently C, O, S, N or NH; and A is hydrogen, hydroxyl, alkyl, alkoxy, hydroxyl-alkyl, halogen, aryl, or

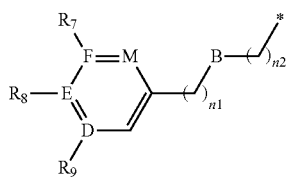

where

B is absent, O, S, or NRa, where Ra is hydrogen or alkyl (e.g., branched or unbranched $C_{1-8}$);

n1 and n2 are the same or different and are 0, 1, 2, 3 or 4;

D, E and F are the same or different and are independently C, N, O or S;

R7, R8, and R9 are the same of different and are independently substituted of unsubstituted alkyl, alkoxy, aryl, acyl, halogenated alkyl, halogenated alkoxy, hydroxylalkyl, O-aryl nitrile, halogen, or hydrogen; and M is absent or CH.

In some aspects, the compound has the structure of formula II:

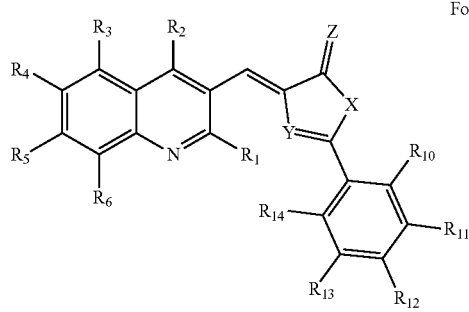

Formula II wherein,

R1 is $OC_nH_{2n+1}$ or $C_nH_{2n+1}$ group;

R2, R3, R4, R5, R6, R10, R11, R12, R13, and R14 are the same of different and are independently substituted of unsubstituted alkyl, alkoxy, aryl, acyl, halogenated alkyl, halogenated alkoxy, hydroxylalkyl, O-aryl nitrile, halogen or hydrogen; and X, Y and Z are the same or different and are independently C, O, S, N or NH.

In some aspects, the compound has the structure of formula III:

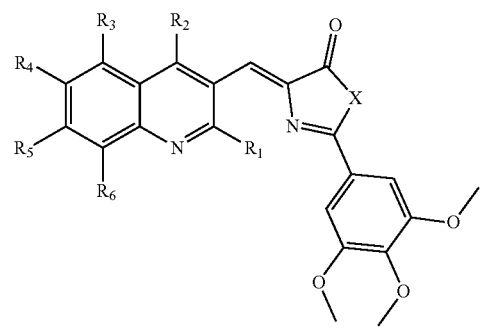

Formula III wherein,

R1 is $OC_nH_{2n+1}$ or $C_nH_{2n+1}$ group

R2, R3, R4, R5, and R6 are the same of different and are independently substituted of unsubstituted alkyl, alkoxy, aryl, acyl, halogenated alkyl, halogenated alkoxy, hydroxylalkyl, O-aryl nitrile, halogen or hydrogen; and X is C, O, S, NH or N.

In some embodiments, the compound of formula III may be a compound having the structure of formula IV:

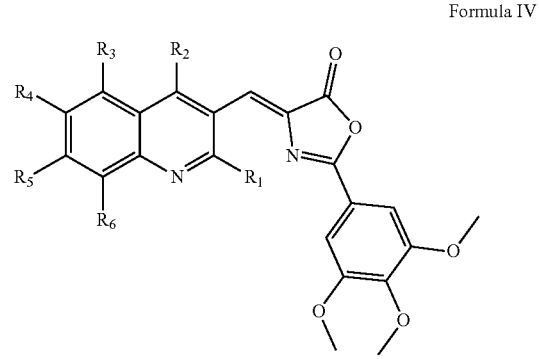

Formula IV wherein,

R1 is $OC_nH_{2n+1}$ or $C_nH_{2n+1}$ group; and

R2, R3, R4, R5, and R6 are the same of different and are independently substituted of unsubstituted alkyl, alkoxy, aryl, acyl, halogenated alkyl, halogenated alkoxy, hydroxylalkyl, O-aryl nitrile, halogen or hydrogen.

In some embodiments, the compound of formula III may be a compound having the structure of formula V:

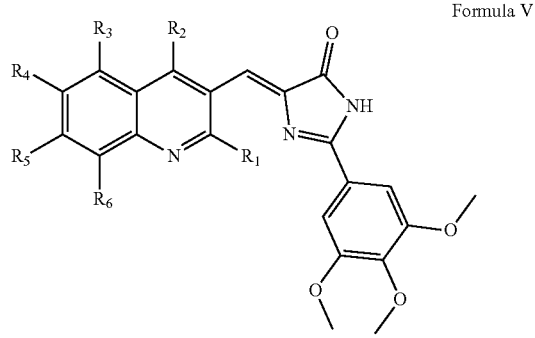
Formula V
wherein,
R1 is $OC_nH_{2n+1}$ or $C_nH_{2n+1}$ group; and
R2, R3, R4, R5, and R6 are the same of different and are independently substituted of unsubstituted alkyl, alkoxy, aryl, acyl, halogenated alkyl, halogenated alkoxy, hydroxylalkyl, O-aryl nitrile, halogen or hydrogen.
In some embodiments, the compound of formula I has any of the following structures:
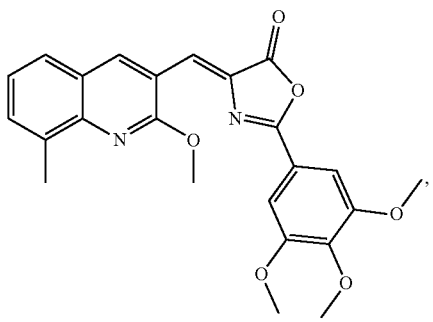
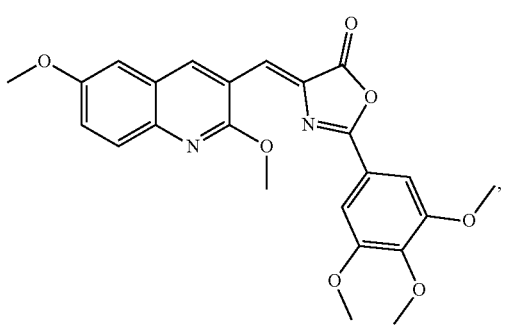
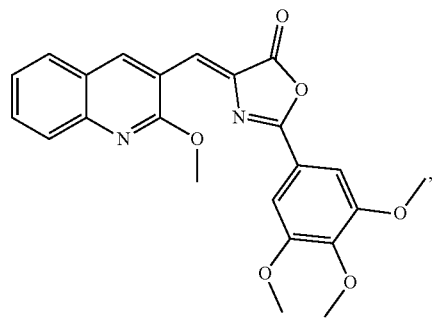
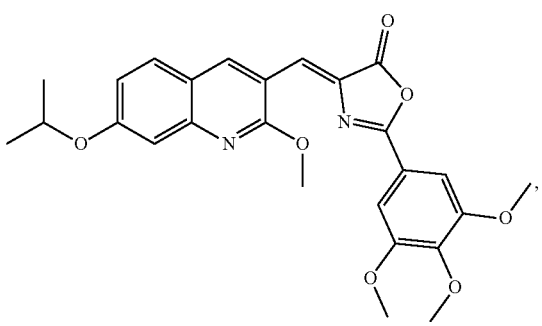
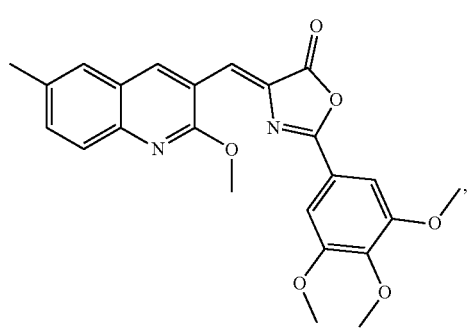
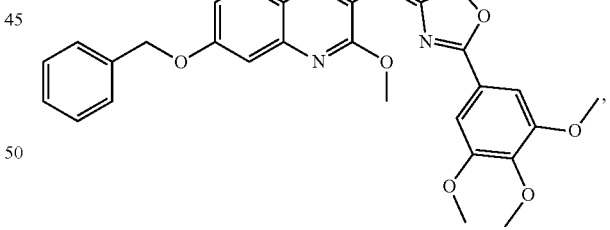
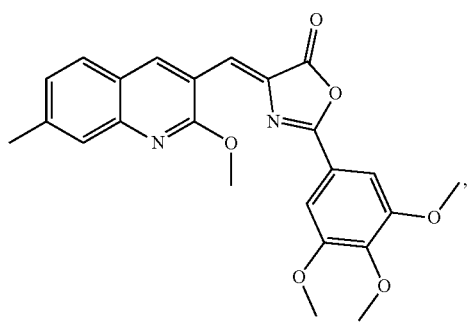
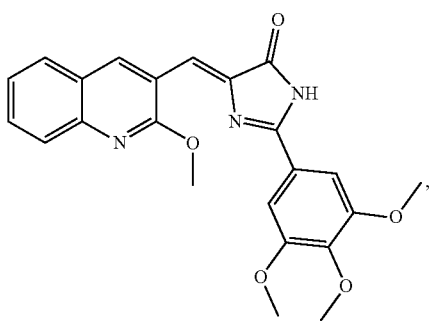

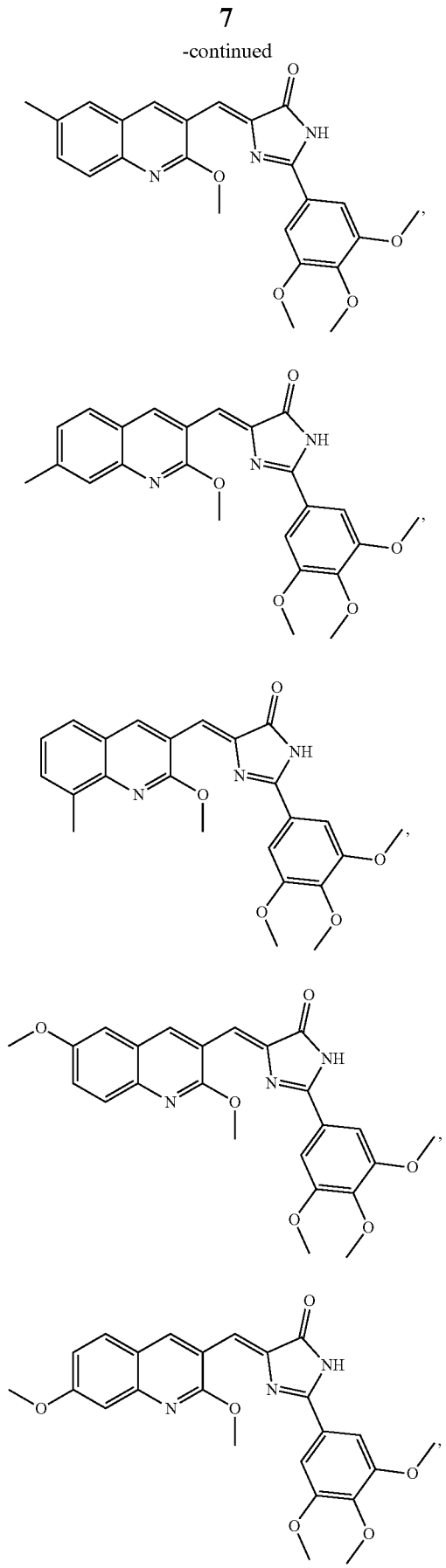
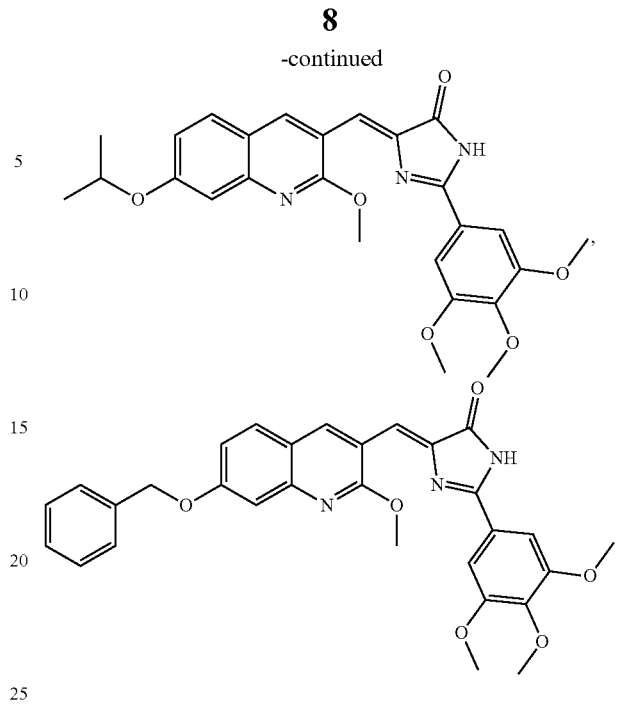

In some embodiments, a pharmaceutical composing the compound of formula 1, or a salt, solvate or hydrate thereof, and a pharmaceutically acceptable carrier are provided.

In some embodiments, a method for treating cancer is provided comprising administering to a subject in need thereof an effective amount of a compound of Formula (I), or a salt, solvate or hydrate thereof.

In some embodiments, the compound of formula I inhibits tubulin polymerization and cell migration, causes G2/M phase arrest, induces apoptosis via a mitochondrial dependent apoptosis pathway, and/or causes reactive oxygen stress generation in the cancer cells.

In some embodiments, the subject is mammalian.

In some embodiments, the subject is human.

In some embodiments, the cancer is selected from the group consisting of but not limited to breast cancer, colon cancer, cervical cancer, or leukemia.

In some embodiments, a method of killing or inhibiting the growth of a cancer stem cell is provided, comprising contacting the cancer stem cell with an effective amount of the compound of Formula (I), or a salt, solvate or hydrate thereof.

In some embodiments, the cancer stem cell is mammalian.
In some embodiments, the cancer stem cell is human.
In some embodiments, the cancer stem cell is in vitro.
In some embodiments, the cancer stem cell is in vivo.
In some embodiments, the cancer stem cell is from a cancer selected from the group consisting of breast cancer, colon cancer, cervical cancer, or leukemia.

BRIEF DESCRIPTION OF THE DRAWINGS

FIG. 3A shows the effect of compound 5c at different time points on apoptosis in MCF-7 cells analysed by flow cytometry after double staining of the cells with Annexin-V-FITC and PI. MCF-7 cells treated with 50 and 250 nM of compound 8c and 50 nM of CA-4 for 24 h, 48 h and 72 h and collected and processed for analysis.

FIGS. 3B-3D show quantitative Quantitative analysis of apoptosis at 24, 48, and 72 hours, respectively. Values represent the mean±SEM for three independent experiments. Statistical analysis was performed using two-way ANOVA (*, p<0.05, p<0.01; *, p<0.001).

FIG. 8A shows an assessment of mitochondrial membrane potential ($\Delta\psi_{mt}$) after treatment of MCF-7 cells with 8c. Cells were treated with indicated concentration of compound 8c for 6, 12 and 24 h and then stained with fluorescent DiOC2(3) for analysis of mitochondrial potential.

DETAILED DESCRIPTION

Figure 1:
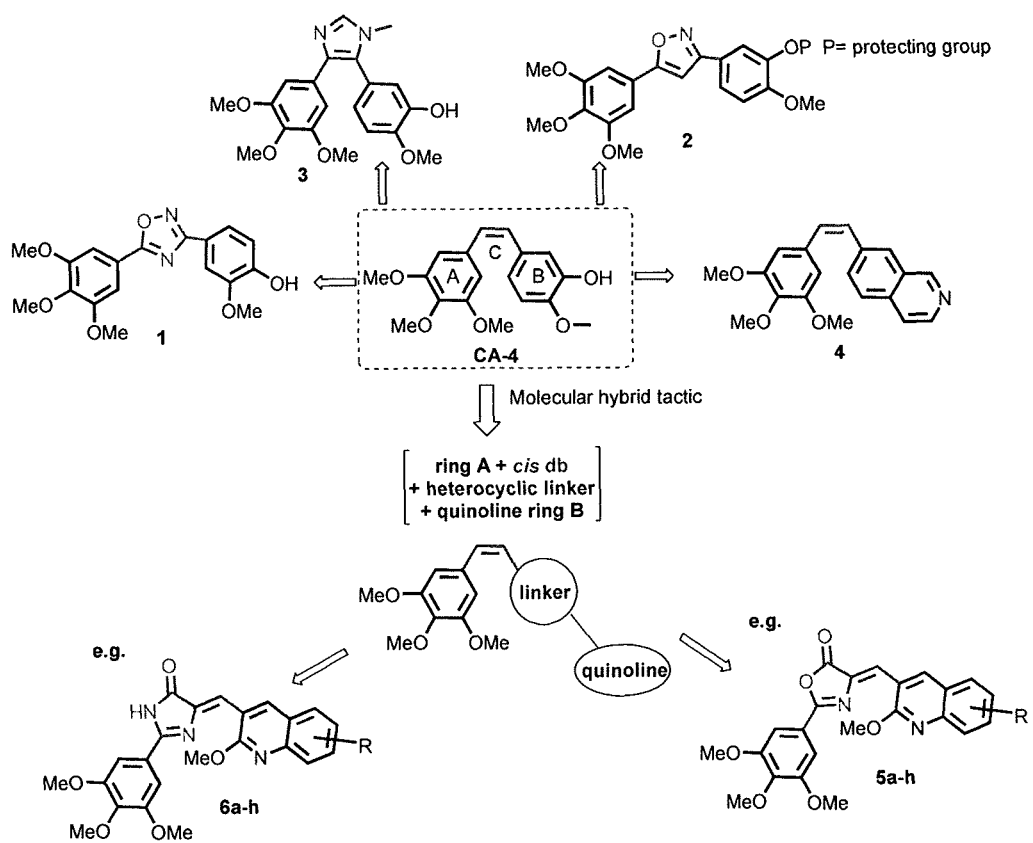
FIG. 1 shows the structure of exemplary CA-4 related analogs, together with examples of our rationalized compounds. Compounds 1, 2, and 3, respectively show oxadiazole, isoxazole and imidazole analogs. Compound 4 is a quinoline analog. Compounds 8a-h and 9a-h are examples of the rationalized compounds of the present invention.

The following descriptions and examples illustrate some exemplary embodiments of the disclosed invention in detail. Those of the skill in the art will recognize that there are numerous variations and modifications of this invention that are encompassed by its scope. Accordingly, the description of a certain exemplary embodiment should not be deemed to limit the scope the present invention.

As described herein, the invention comprises vinylquinoline derivatives and potential therapeutics for different form of cancers. Particular cancers which can be treated with the vinylquinoline derivatives include but are not limited to breast cancer, colon cancer, cervical cancer and leukemia. Other exemplary cancers which may be treated with the vinylquinoline deriatives are described below.

Definitions

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. In embodiments, the cancer is a cancer that metastasized to bone. In embodiments, the cancer is prostate cancer, such as prostate cancer-derived bone metastasis.

As used herein, any "R" group(s) such as, without limitation, R, R1, R2, R3, R4, R5, R6, R7, R8, R9, R10 and so on represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. R groups at different locations may be the same or different.

As used herein, any "Z", "Y", "X" or "A" group(s) represent substituents that can be attached to the indicated atom. Z, Y, X or A group may be substituted or unsubstituted. Z, Y, X, A groups at different locations may be the same or different.

As used herein, "alkyl" refers to a straight or branched hydrocarbon chain that includes a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "C1-C6 alkyl" or similar designations. By way of example only, "C1-C6 alkyl" indicates that there are one to four carbon atoms in the alkyl chain, i.e., the alkyl chain is selected from methyl, ethyl, propyl, isopropyl, n-butyl, isobutyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkoxy" refers to the formula —OR wherein R is an alkyl, an alkenyl, an alkynyl, a cycloalkyl, a cycloalkenyl or a cycloalkynyl is defined as above. A non-limiting list of alkoxys is methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a C6 aryl group. Examples of aryl groups include, but are not limited to, benzene, naphthalene and azulene. An aryl group may be substituted or unsubstituted.

As used herein, "acyl" refers to a hydrogen, alkyl, alkenyl, alkynyl, or aryl connected, as substituents, via a carbonyl group. Examples include but are not limited to formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxy ethyl. A hydroxyalkyl may be substituted or unsubstituted.

As used herein, "halogenated alkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "halogenated alkoxy" refers to an alkoxy group in which one or more of the hydrogen atoms are replaced by a halogen (e.g., mono-haloalkoxy, di-haloalkoxy and tri-haloalkoxy, etc.). Such groups include but are not limited to, chloromethoxy, fluoromethoxy, difluoromethoxy, trifluoromethoxy, 1-chloro-2-fluoromethoxy, and 2-fluoroisobutoxy. A haloalkoxy may be substituted or unsubstituted.

As used herein, "vinylquinoline" is an alkene conjugated to a quinoline.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "C1-C3 alkoxyphenyl" may include one or more of the same or different alkoxy groups containing, for example, one, two or three atoms.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvates forms with pharmaceutically acceptable solvents such as water, ethanol, or the like. In other embodiments, the compounds described herein exist in unsolvated form. Solvates contain either stoichiometric or non-stoichiometric amounts of a solvents and may be formed during the process of crystallization with pharmaceutically acceptable solvent such as water, ethanol, or the like. Hydrates are formed when the solvent is water, or alcoholates are formed when the solvent is alcohol. In addition, the compound provided herein can exist in unsolvated as well as solvated forms. In general, the solvated forms are considered equivalent to the unsolvated form for the purpose of the compounds and methods provided herein.

Where a range of values is provided, it is understood that the upper and lower limit, and each intervening value between the upper and lower limit of the range is encompassed within the embodiments.

Certain Synthetic Methods

In some embodiments, the synthesis of compounds of formula I comprise two core structural elements: (i) 2-methoxyquinolyl-3-carbaldehyde moiety, and (ii) 3,4,5-trimethoxyphenyl moiety. For core one, a concise (three-step) synthesis leading to 2-methoxyquinoline-3-carbaldehyde derivatives 4 as shown in (Scheme 1). This began with acetylation of the appropriate aniline derivatives 1 under typical condition using glacial acetic acid and acetic anhydride at 0° C. temperature. The produced amides 2 were subjected to a Vilsmeier-Haack reaction to give the 2-Chloroquinolone-3-carbaldehyde derivatives 3. Installing the important methoxy substituent to the later compounds has been achieved through using sodium methoxide at 40° C. in methanol which then led to the formation of aldehydes 4 [31] [32]

Similarly, another acylation has been established for the starting material acid 5 under highly acidic condition using $SOCl_2$ to deliver the acyl benzotriazole 6 (Scheme 2). Unlike halogens, the benzotriazole group rarely leaves if there is no hetero-atom at the α-carbon atom. Herein, the advantage of using benzotriazole is of being the direct attachment to the carbonyl group that forms N-acylbenzotriazole synthon. In general, this synthon is classified as an efficient N-acylating reagent [33].

Certain compounds provided herein can be prepared according to the following schemes 1 and 2.

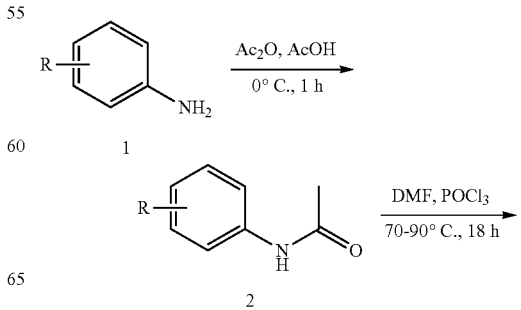

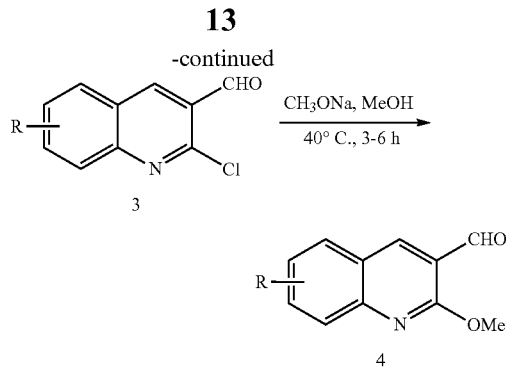

wherein,

R represents one or more R groups which are the same of different and each of which is independently, substituted of unsubstituted, alkyl, alkoxy, aryl, acyl, halogenated alkyl, halogenated alkoxy, hydroxylalkyl, O-aryl nitrile, halogen or hydrogen Scheme 1

Following the next step, treatment of acyl benzotriazole 6 with glycine in aqueous acetonitrile gave the acyl glycine 7. Engagement of the later compound to a condensation reaction with the appropriate quinoline aldehydes 4 in the presence of acetic anhydride and catalytic amount of sodium acetate furnished oxazolones of formula IV. Aminolysis of the last compounds via condensation reaction with ammonia led to the formation of the desired imidazolones of formula V. It seems that ammonia, as a nucleophile, attacks the carbonyl group of the oxazolone ring, this was followed by immediate intramolecular condensation and thus cyclization has been occurred to deliver the imidazolones. $^1$H NMR spectra of compounds of formula V showed a common singlet signal at δ 12.03-12.22 ppm as an indication to the presence of NH moiety. Moreover, noticeable signals of three methoxy groups of ring A at δ 3.93-3.99 and 3.79-3.80 ppm, as well as characteristic singlet signal due to methoxy group at δ 4.04-4.11 ppm at quinoline ring B. In general, $^{13}$C NMR spectra of the alkenyl and aromatic carbons for all of the synthesized compounds were appeared at their anticipated chemical shifts.

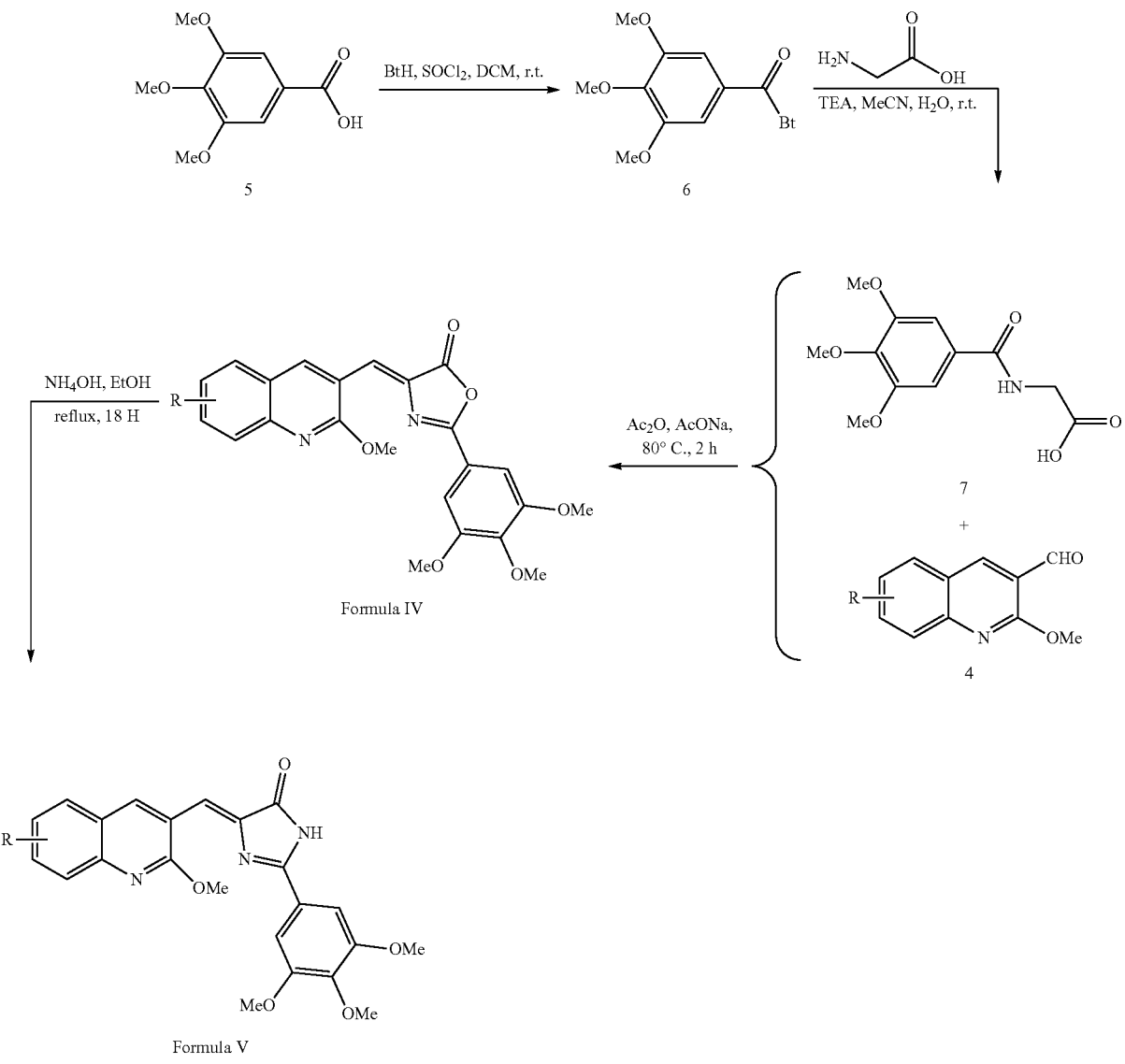

wherein,

R represents one or more R groups which are the same of different and each is independently substituted of unsubstituted alkyl, alkoxy, aryl, acyl, halogenated alkyl, halogenated alkoxy, hydroxylalkyl, O-aryl nitrile, halogen or hydrogen Scheme 2

Exemplary Compounds

Certain compounds provided herein include compounds having a formula:

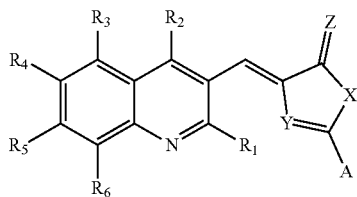

Formula I wherein,

R1 is $OC_nH_{2n+1}$ or $C_nH_{2n+1}$ group;

R2, R3, R4, R5 and R6 are the same of different and are independently substituted of unsubstituted alkyl, alkoxy, aryl, acyl, halogenated alkyl, halogenated alkoxy, hydroxylalkyl, O-aryl nitrile, halogen or hydrogen;

X, Y and Z are the same or different and are independently C, O, S, N or NH; and A is hydrogen, hydroxyl, alkyl, alkoxy, hydroxyl-alkyl, halogen, aryl, or

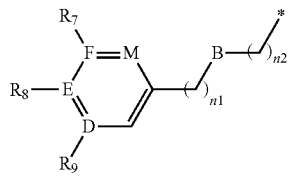

where, B is absent, O, S, or NRa, where Ra is hydrogen or alkyl;

n1 and n2 are the same or different and are 0, 1, 2, 3 or 4;

D, E and F are the same or different and are independently C, N, O, or S;

R7, R8, and R9 are the same of different and are independently substituted or unsubstituted alkyl, alkoxy, aryl, acyl, halogenated alkyl, halogenated alkoxy, hydroxylalkyl, O-aryl nitrile, halogen or hydrogen; and M is absent or CH.

In some aspects, the compound has the structure of formula II:

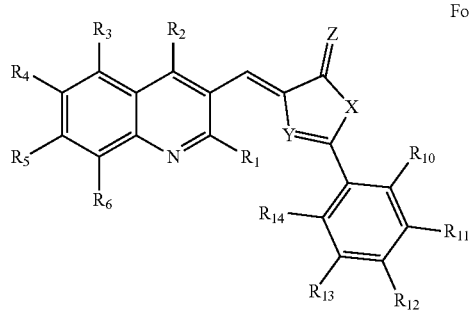

Formula II wherein,

R1 is $OC_nH_{2n+1}$ or $C_nH_{2n+1}$ group;

R2, R3, R4, R5, R6, R10, R11, R12, R13, and R14 are the same of different and are independently substituted of unsubstituted alkyl, alkoxy, aryl, acyl, halogenated alkyl, halogenated alkoxy, hydroxylalkyl, O-aryl nitrile, halogen or hydrogen; and X, Y and Z are the same or different and are independently C, O, S, N or NH.

In some aspects, the compound has the structure of formula III:

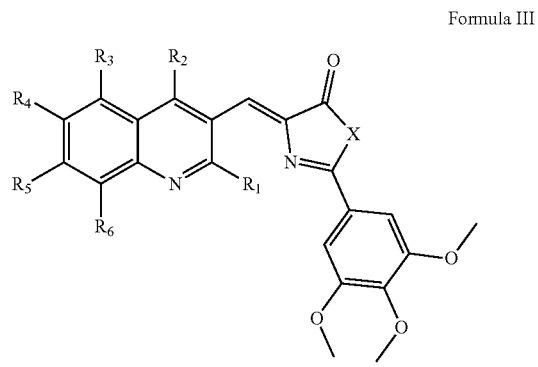

Formula III wherein,

R1 is $OC_nH_{2n+1}$ or $C_nH_{2n+1}$ group

R2, R3, R4, R5, and R6 are the same of different and are independently substituted of unsubstituted alkyl, alkoxy, aryl, acyl, halogenated alkyl, halogenated alkoxy, hydroxylalkyl, O-aryl nitrile, halogen or hydrogen; and X is C, O, S, NH or N.

In some embodiments, the compound of formula III may be a compound having the structure of formula IV:

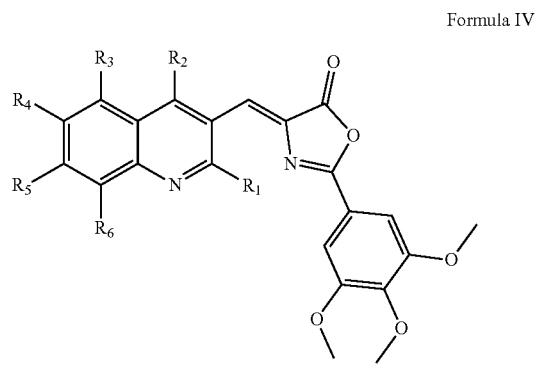

Formula IV wherein,

R1 is $OC_nH_{2n+1}$ or $C_nH_{2n+1}$ group; and

R2, R3, R4, R5, and R6 are the same of different and are independently substituted of unsubstituted alkyl, alkoxy, aryl, acyl, halogenated alkyl, halogenated alkoxy, hydroxylalkyl, O-aryl nitrile, halogen or hydrogen.

In some embodiments, the compound of formula III may be a compound having the structure of formula V:

Formula V
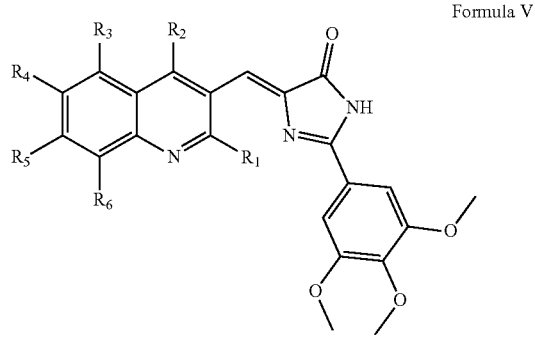
wherein,
R1 is $OC_nH_{2n+1}$ or $C_nH_{2n+1}$ group; and
R2, R3, R4, R5, and R6 are the same of different and are independently substituted of unsubstituted alkyl, alkoxy, aryl, acyl, halogenated alkyl, halogenated alkoxy, hydroxylalkyl, O-aryl nitrile, halogen or hydrogen.
In some embodiments, the compound of formula I has any of these formulas:
8a
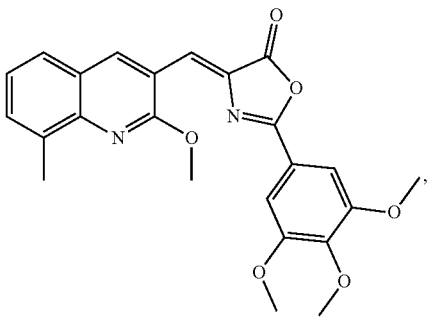
8b
8c
8d
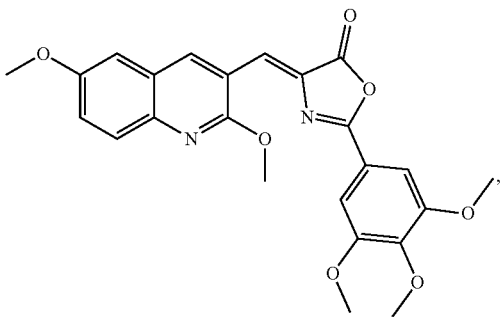
8e
8f
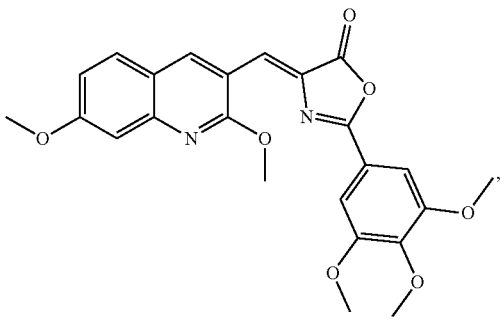
8g
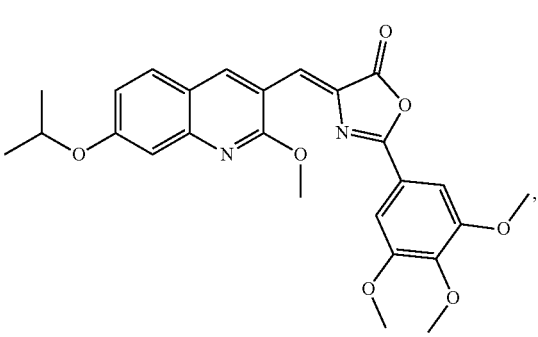
8h
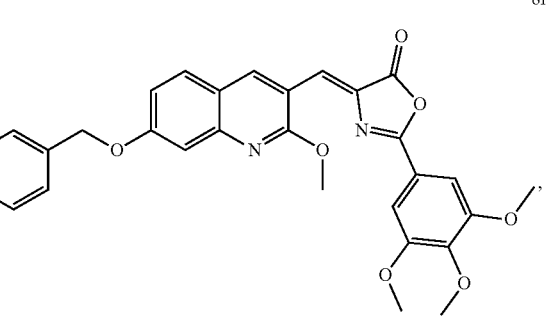

-continued

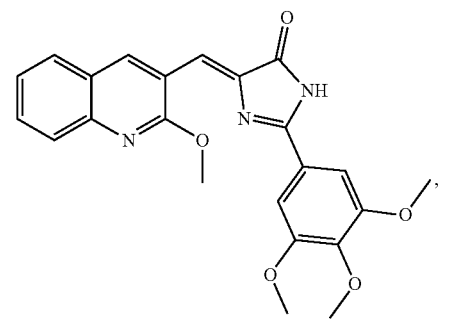
9a

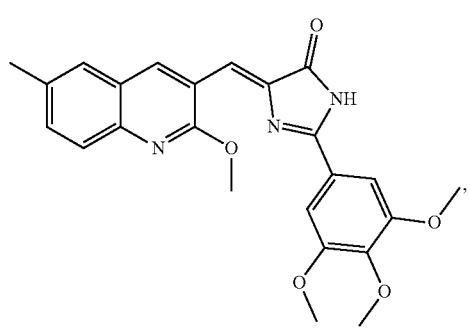
9b

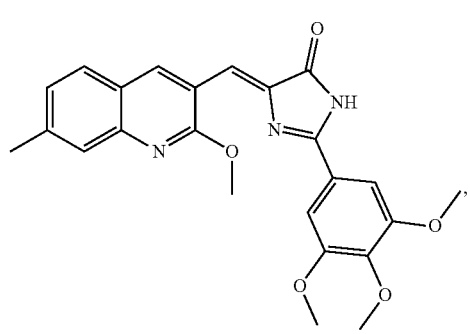
9c

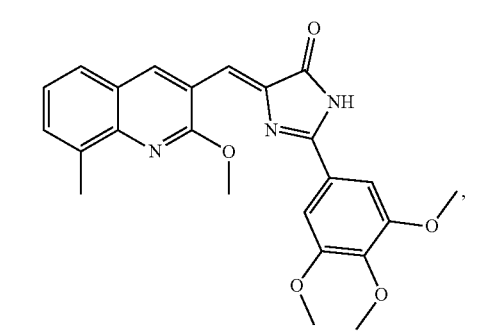
9d

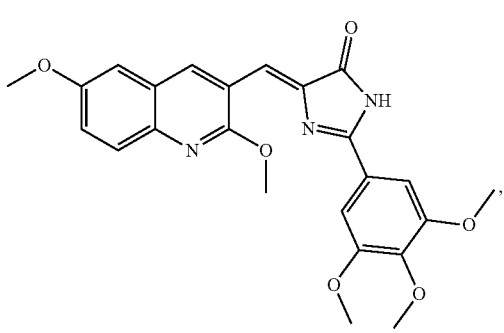
9e

-continued

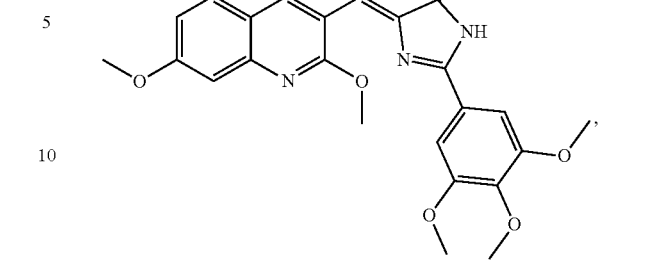
9f

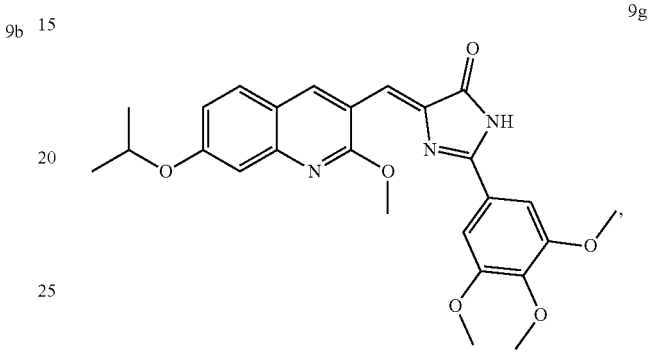
9g

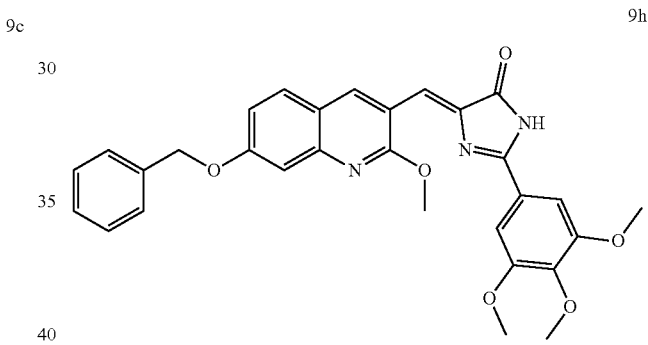
9h

The compounds can be in the form of a pharmaceutically acceptable salt. The term "pharmaceutically acceptable salt" as used herein is a broad term, and is to be given its ordinary and customary meaning to a person of ordinary skill in the art (and is not to be limited to a special or customized meaning), and refers without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity.

The compounds can be in amorphous form, or in crystalline forms. The crystalline forms of the compounds can exist as polymorphs, which are included in preferred embodiments. In addition, some of the compounds may also form solvates or hydrates with water or other organic solvents. Such solvates are similarly included within the scope of the disclosure.

The compounds of preferred embodiments include isomers, racemates, optical isomers, enantiomers, diastereomers, tautomers, and cis/trans conformers. All such isomeric forms are included within preferred embodiments, including mixtures thereof. As discussed above, the compounds of preferred embodiments may have chiral centers, for example, they may contain asymmetric carbon atoms and may thus exist in the form of enantiomers or diastereoisomers and mixtures thereof, e.g., racemates. Asymmetric carbon atom(s) can be present in the (R)-, (S)-, or (R,S)-configuration, preferably in the (R)- or (S)-configuration, or can be present as mixtures. Isomeric mixtures can be separated, as desired, according to conventional methods to obtain pure isomers.

The compounds can be in amorphous form, or in crystalline forms. The crystalline forms of the compounds of preferred embodiments can exist as polymorphs, which are included in preferred embodiments. In addition, some of the compounds of preferred embodiments may also form solvates with water or other organic solvents. Such solvates are similarly included within the scope of the preferred embodiments.

Certain Pharmaceutical Compositions

It is generally preferred to administer the compounds in an intravenous or subcutaneous unit dosage form; however, other routes of administration are also contemplated. Contemplated routes of administration include but are not limited to oral, parenteral and intratumoral. The compounds can be formulated into liquid preparations for, e.g., oral administration. Suitable forms include suspensions, syrups, elixirs, and the like. Particularly preferred unit dosage forms for oral administration include tablets and capsules. Unit dosage forms configured for administration once a day are particularly preferred; however, in certain embodiments it can be desirable to configure the unit dosage form for administration twice, or more, a day; every other day; or three times a week; or once a week.

The pharmaceutical compositions are preferably isotonic with the blood or other body fluid of the recipient. The isotonicity of the compositions can be attained using sodium tartrate, propylene glycol or other inorganic or organic solutes. Sodium chloride may be preferred in some embodiments. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents.

A pharmaceutically acceptable preservative can be employed to increase the shelf life of the pharmaceutical compositions. Benzyl alcohol can be suitable, although a variety of preservatives including, for example, parabens, thimerosal, chlorobutanol, or benzalkonium chloride can also be employed. A suitable concentration of the preservative is typically from about 0.02% to about 2% based on the total weight of the composition, although larger or smaller amounts can be desirable depending upon the agent selected. Reducing agents, as described above, can be advantageously used to maintain good shelf life of the formulation.

The compounds can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, coloring agents, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; $18^{th}$ and $19^{th}$ editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions can be provided as a tablet, aqueous or oil suspension, dispersible powder or granule, emulsion, hard or soft capsule, syrup or elixir. Compositions intended for oral use can be prepared according to any method known in the art for the manufacture of pharmaceutical compositions and can include one or more of the following agents: sweeteners, flavoring agents, coloring agents and preservatives. Aqueous suspensions can contain the active ingredient in admixture with excipients suitable for the manufacture of aqueous suspensions.

Formulations for oral use can also be provided as hard gelatin capsules, wherein the active ingredient(s) are mixed with an inert solid diluent, such as calcium carbonate, calcium phosphate, or kaolin, or as soft gelatin capsules. In soft capsules, the compounds can be dissolved or suspended in suitable liquids, such as water or an oil medium, such as peanut oil, olive oil, fatty oils, liquid paraffin, or liquid polyethylene glycols. Stabilizers and microspheres formulated for oral administration can also be used. Capsules can include push-fit capsules made of gelatin, as well as soft, sealed capsules made of gelatin and a plasticizer, such as glycerol or sorbitol. The push-fit capsules can contain the active ingredient in admixture with fillers such as lactose, binders such as starches, and/or lubricants such as talc or magnesium stearate and, optionally, stabilizers.

Tablets can be uncoated or coated by known methods to delay disintegration and absorption in the gastrointestinal tract and thereby provide a sustained action over a longer period of time. For example, a time delay material such as glyceryl monostearate can be used. When administered in solid form, such as tablet form, the solid form typically comprises from about 0.001 wt. % or less to about 99 wt. % or more of active ingredient(s), preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, 45, 50, 55, 60, 65, 70, 75, 80, 85, 90, 95 or more wt.

Tablets can contain the active ingredients in admixture with non-toxic pharmaceutically acceptable excipients including inert materials. For example, a tablet can be prepared by compression or molding, optionally, with one or more additional ingredients. Compressed tablets can be prepared by compressing in a suitable machine the active ingredients in a free-flowing form such as powder or granules, optionally mixed with a binder, lubricant, inert diluent, surface active or dispersing agent. Molded tablets can be made by molding, in a suitable machine, a mixture of the powdered inhibitor moistened with an inert liquid diluent.

Preferably, each tablet or capsule contains from about 0.1 mg or less to about 1,000 mg or more of at least one compound, more preferably from about 10, 20, 30, 40, 50, 60, 70, 80, 90, or 100 mg to about 150, 200, 250, 300, 350, 400, 450, 500, 550, 600, 650, 700, 750, 800, or 900 mg. Most preferably, tablets or capsules are provided in a range of dosages to permit divided dosages to be administered. A dosage appropriate to the patient and the number of doses to be administered daily can thus be conveniently selected. In certain embodiments it can be preferred to incorporate two or more of the therapeutic agents to be administered into a single tablet or other dosage form (e.g., in a combination therapy); however, in other embodiments it can be preferred to provide the therapeutic agents in separate dosage forms. Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents can be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragacanth, or alginic acid or salts thereof.

Binders can be used to form a hard tablet. Binders include materials from natural products such as acacia, tragacanth, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, can be included in tablet formulations.

Surfactants can also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations can be employed wherein the analog(s) thereof is incorporated into an inert matrix that permits release by either diffusion or leaching mechanisms. Slowly degenerating matrices can also be incorporated into the formulation. Other delivery systems can include timed release, delayed release, or sustained release delivery systems.

Coatings can be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments can be added for identification or to characterize different combinations of inhibitor doses When administered orally in liquid form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

Pulmonary delivery can also be employed. The compound is delivered to the lungs while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of compound. Typically, each formulation is specific to the type of device employed and can involve the use of an appropriate propellant material, in addition to diluents, adjuvants, and/or carriers useful in therapy.

The compound and/or other optional active ingredients are advantageously prepared for pulmonary delivery in particulate form with an average particle size of from 0.1μιη or less to 10 μιη or more, more preferably from about 0.2, 0.3, 0.4, 0.5, 0.6, 0.7, 0.8, or 0.9μιη to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5μιη. Pharmaceutically acceptable carriers for pulmonary delivery of inhibitor include carbohydrates such as trehalose, mannitol, xylitol, sucrose, lactose, and sorbitol. Other ingredients for use in formulations can include DPPC, DOPE, DSPC, and DOPC. Natural or synthetic surfactants can be used, including polyethylene glycol and dextrans, such as cyclodextran. Bile salts and other related enhancers, as well as cellulose and cellulose derivatives, and amino acids can also be used. Liposomes, microcapsules, microspheres, inclusion complexes, and other types of carriers can also be employed.

Pharmaceutical formulations suitable for use with a nebulizer, either jet or ultrasonic, typically comprise the inhibitor dissolved or suspended in water at a concentration of about 0.01 or less to 100 mg or more of inhibitor per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg per mL of solution. The formulation can also include a buffer and a simple sugar (e.g., for protein stabilization and regulation of osmotic pressure). The nebulizer formulation can also contain a surfactant, to reduce or prevent surface induced aggregation of the inhibitor caused by atomization of the solution in forming the aerosol.

Formulations for use with a metered-dose inhaler device generally comprise a finely divided powder containing the active ingredients suspended in a propellant with the aid of a surfactant. The propellant can include conventional propellants, such as chlorofluorocarbons, hydrochlorofluorocarbons, hydrofluorocarbons, and hydrocarbons. Preferred propellants include trichlorofluoromethane, dichlorodifluoromethane, dichlorotetrafluoroethanol, 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing inhibitor, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

When a compound of the preferred embodiments is administered by intravenous, parenteral, or other injection, it is preferably in the form of a pyrogen-free, parenterally acceptable aqueous solution or oleaginous suspension. Suspensions can be formulated according to methods well known in the art using suitable dispersing or wetting agents and suspending agents. The preparation of acceptable aqueous solutions with suitable pH, isotonicity, stability, and the like, is within the skill in the art. A preferred pharmaceutical composition for injection preferably contains an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils can be employed conventionally as a solvent or suspending medium. For this purpose, any bland fixed oil can be employed including synthetic mono or diglycerides. In addition, fatty acids such as oleic acid can likewise be used in the formation of injectable preparations. The pharmaceutical compositions can also contain stabilizers, preservatives, buffers, antioxidants, or other additives known to those of skill in the art.

The duration of the injection can be adjusted depending upon various factors, and can comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

The compounds can additionally employ adjunct components conventionally found in pharmaceutical compositions in their art-established fashion and at their art-established levels. Thus, for example, the compositions can contain additional compatible pharmaceutically active materials for combination therapy (such as supplementary antimicrobials, antipruritics, astringents, local anesthetics, anti-inflammatory agents, reducing agents, chemotherapeutics and the like), or can contain materials useful in physically formulating various dosage forms of the preferred embodiments, such as excipients, dyes, thickening agents, stabilizers, preservatives or antioxidants. Anti-cancer agents that can be used in combination with the compounds of preferred embodiments include, but are not limited to, vinca alkaloids such as vinblastine and vincristine; anthracyclines such as doxorubicin, daunorubicin, epirubicin; anthracenes such as bisantrene and mitoxantrone; epipodophyllo-toxins such as etoposide and teniposide; and other anticancer drugs such as actinomyocin D, mithomycin C, mitramycin, methotrexate, docetaxel, etoposide (VP-16), paclitaxel, docetaxel, and adriamycin); and immunosuppressants (e.g., cyclosporine A, tacrolimus).

Therapeutic Methods

Some embodiments provided herein relate to methods of treating cancer such as but not limited to breast cancer, colon cancer, cervical cancer and leukemia. Other cancers which may be treated are set forth above in the definitions section. In general, the methods involve administering an effective amount of a compound of formula I or a pharmaceutically acceptable salt, solvate or hydrate thereof, to a subject in need thereof. The subject may be a mammal, such as a human, but veterinary usage is also encompassed. The cancer that is treated can be any type of cancer, and the treatment can be sufficient to alleviate the symptoms of the cancer, halt expansion and growth of the cancer, cause remission of the cancer, etc.

Also provided are methods of killing or inhibiting the growth of cancer stem cells. The methods generally comprising a step of contacting a cancer stem cell with an amount of the compound of Formula (I) that is sufficient to kill or inhibit the growth of the cell. The cancer stem cell may be mammalian, e.g. human, and may be in vitro or in vivo, and may be from any type of cancer, examples of which include but are in no way limited to breast cancer, colon cancer, cervical cancer and leukemia.

Exemplary quinoline compounds, as shown in FIG. 1, are arranged into two distinct structural groups with modifications in the ethylene bridge. All the synthesised compounds were first evaluated for their antiproliferative activity against four representative cancer cell lines including MCF-7 breast, HL-60 leukemia, HCT-116 colon and HeLa cervical cancer cells and compared with CA-4 as reference compound using the MTT assay. The results are shown in table 1. It is evident that the majority of the target compounds displayed moderate to potent antiproliferative activity in these cell lines.

The first series of analogues 8a-8h examined contained an oxazolone ring in addition to a number of different substituents on the quinoline ring. Among the oxazolone containing compounds, compound 8a bearing no substituent in the quinoline ring was the least active in this series. The relative position of methyl substituent on quinoline ring seemed to be critical for antiproliferative activity. Compound 8c (containing methyl group in the 7-position of the quinoline ring) displayed impressive potency comparable with CA-4 in nanomolar range against all four cell lines ($IC_{50}$ values in HL-60, MCF-7, HCT-116 and HeLa cancer cells were 19.1, 10.7, 22.5 and 42.7 nM respectively). In contrast, both the 6-$CH_3$ analog (8b) and 8-$CH_3$ analog (8d) were from 3- to 15-fold less active than 8c. Generally, the nature of the substituents on the quinoline ring of the oxazolone significantly influenced the biological activity. Replacement of the methyl group with the stronger electron-releasing methoxy group (compounds 8b and 8c with 8e and 8f, respectively) impacted on the antiproliferative activity; methoxy-containing 8e was from 2.7- to 13 fold more active than methyl-containing 8b on the four cancer cell lines while 8f was equipotent to 8c against two cells lines MCF-7 and HCT-116 with reduction in activity against the other cancer cell lines HL-60 and HeLa. Specifically, the $IC_{50}$ values for compound 8e were 68.5, 56.8, 31.8 and 10.1 in HL-60, MCF-7, HCT-116 and HeLa cancer cells, respectively. Larger substituents at the quinoline ring as in 8g (7-tert-butyl) and 8h (7-benzyloxy) led to a dramatic decrease in activity compared to their corresponding analogue 8f (7-methoxy). Based on the results, it can be concluded that the presence of a variety of smaller and polar groups are favourable on the quinoline ring of the oxazolone analogues to maintain the antiproliferative activity.

Another exemplary series of quinoline compounds containing imidazolone cyclic moiety as a bioisostere of the oxazolone linker was synthesised. In general, Introduction of imidazolone of the quinoline analogues with a range of different substituents at quinoline ring e.g. 9a-9h resulted in an impressive antiproliferative activity. As shown in table 1, it is observed there is a less considerable difference in potency between imidazolone and oxazolone derivatives in all four cell lines which could be due to the similar electronic effect. An opposite effect occurred with deletion of methyl substituent on the quinoline ring to furnish compound 9a, which led to reduction of activity with $IC_{50}$ values more than 1 µM in four cell lines which is in agreement with the results obtained for the oxzolone derivative (8a). Imidazolone compounds with methyl substituents at different position on the quinoline ring e.g. 6-$CH_3$ (9b), 7-$CH_3$ (9c) and 8-$CH_3$ (9d) displayed potent activity in submicromolar range in all four cancer cell lines studied.

ably, both oxazolone and imidazolone compounds bearing a quinoline ring displayed potent antiproliferative effects, strengthening our hypothesis that nitrogen-containing heterocycles, such as quinoline, are beneficial surrogates for the 3-hydroxy-4-methoxyphenyl ring of CA-4. Due to impressive antiproliferative potency of compound 8c (containing methyl group in the 7-position of the quinoline ring), it was selected for further molecular biochemical investigations in MCF-7 cells.

Previous studies revealed that the trimethoxyphenyl (TMP) containing stilbenoid derived tubulin inhibitors that bind at the colchicine site, such as colchicine and CA-4, resulting in microtubule depolymerization [34, 35]. To confirm whether the quinoline compounds could target the tubulin-microtubule system, representative quinoline compounds include four oxazolone analogues (8a, 8c, 8e and 8g) and two imidazolone analogues (9c and 9e), as well as reference compound CA-4, were evaluated for their antitubulin polymerization activities as presented in Table 2. In oxazolone compounds, methyl analogue 8c and methoxy analogue 8e strongly inhibited tubulin assembly with activities superior or comparable ($IC_{50}$: 1.2 and 2.2 µM) to that of CA-4 ($IC_{50}$: 2.1 µM), while unsubstituted analogue 8a ($IC_{50}$: 13.9 µM) and tert-butyl analogue 8g were 4 and 6-fold less

TABLE 1

Antiproliferative activity of quinoline analogues against human cancer cell lines ($IC_{50}$ [µM])

| Compound no. | X | R | $IC_{50}$ value (µM)[a] | | | |
|---|---|---|---|---|---|---|
| | | | HL-60 | MCF-7 | HCT-116 | HeLa |
| 8a | O | H | 3.309 ± 0.022 | 1.712 ± 0.04 | 2.012 ± 0.08 | 2.113 ± 0.034 |
| 8b | O | 6-$CH_3$ | 0.197 ± 0.04 | 0.132 ± 0.013 | 0.184 ± 0.007 | 0.117 ± 0.085 |
| 8c | O | 7-$CH_3$ | 0.019 ± 0.059 | 0.010 ± 0.003 | 0.022 ± 0.0016 | 0.042 ± 0.0015 |
| 8d | O | 8-$CH_3$ | 0.268 ± 0.093 | 0.154 ± 0.071 | 0.191 ± 0.001 | 0.153 ± 0.083 |
| 8e | O | 6-$OCH_3$ | 0.068 ± 0.034 | 0.056 ± 0.027 | 0.031 ± 0.0014 | 0.010 ± 0.004 |
| 8f | O | 7-$OCH_3$ | 0.352 ± 0.021 | 0.052 ± 0.0021 | 0.066 ± 0.005 | 0.138 ± 0.026 |
| 8g | O | 7-$OCH(CH_3)_2$ | 1.822 ± 0.64 | 1.507 ± 0.22 | 7.880 ± 0.3 | 1.747 ± 0.5 |
| 8h | O | 7-$OCH_2Ph$ | 4.66 ± 0.26 | 1.932 ± 0.61 | 1.563 ± 0.72 | 1.054 ± 0.84 |
| 9a | NH | H | 1.561 ± 0.055 | 1.033 ± 0.055 | 8.21 ± 0.0077 | 1.409 ± 0.096 |
| 9b | NH | 6-$CH_3$ | 0.240 ± 0.012 | 0.063 ± 0.0011 | 0.173 ± 0.025 | 0.188 ± 0.013 |
| 9c | NH | 7-$CH_3$ | 0.661 ± 0.026 | 0.223 ± 0.056 | 0.284 ± 0.083 | 0.733 ± 0.091 |
| 9d | NH | 8-$CH_3$ | 0.096 ± 0.0063 | 0.137 ± 0.023 | 0.109 ± 0.011 | 0.126 ± 0.044 |
| 9e | NH | 6-$OCH_3$ | 0.272 ± 0.05 | 0.042 ± 0.0025 | 0.085 ± 0.003 | 0.062 ± 0.0037 |
| 9f | NH | 7-$OCH_3$ | 0.210 ± 0.098 | 0.092 ± 0.0062 | 0.187 ± 0.009 | 0.101 ± 0.09 |
| 9g | NH | 7-$OCH(CH_3)_2$ | 5.114 ± 0.41 | 5.562 ± 0.13 | 1.620 ± 0.95 | 4.439 ± 0.6 |
| 9h | NH | 7-$OCH_2Ph$ | 4.93 ± 0.26 | 1.695 ± 0.82 | 2.610 ± 0.43 | 2.070 ± 0.39 |
| CA-4 | — | — | 0.076 ± 0.004 | 0.019 ± 0.004 | 0.026 ± 0.001 | 0.064 ± 0.004 |

[a]$IC_{50}$ values are half maximal inhibitory concentrations required to block the growth stimulation of cells. Values represent the mean for three experiments performed in triplicate.

The position of the methoxy substituent on the quinoline heterocycle significantly influenced the antiproliferative activity against the four selected cancer cell lines. For example, the antiproliferative activity of 6-methoxy-substituted (9e) was better than its analogue 7-methoxy-substituted (9f) against MCF-7, HCT-116 and HeLa with $IC_{50}$ values of 42.9, 85.0 and 62.3 nM for 9e compared to 92.7, 187.9 and 101.1 nM for 9f, respectively but exhibited less antiproliferative activity in HL-60 with $IC_{50}$ value of 272 nM for 9e. In similar trends for oxazolone derivatives, bulky substituents on the quinoline ring 9g (7-tert-butyl) and 9h (7-benzyloxy) resulted in drastic decrease in activity in all the four cancer cell lines with 14-125 fold loss in potency compared to their corresponding 9f (7-methoxy) containing compounds, respectively Different substituents on the quinoline ring may affect the interaction with surrounding residues of tubulin. Remarkably, both oxazolone and imidazolone compounds bearing a active than CA-4 respectively. In imidazolone compounds, 9e was superior tubulin polymerization inhibition compared to CA-4 with $IC_{50}$=1.4 µM. Methyl analogue 9c was inactive in the tubulin polymerization assay ($IC_{50}$=20.2 µM) and is 16-fold less active to its oxazolone derivative 8c which is in agreements with the poor cell growth inhibitory activity of 9c ($IC_{50}$: 22.3-73.3 µM) against the panel of cancer cells.

8c compound was also examined at two different concentrations (1 and 5 µM) for their ability to compete with colchicine for binding to tubulin using a [$^3$H] colchicine binding assay. The most potent inhibitors of tubulin polymerization compound 8c was strongly inhibited [$^3$H]-colchicine binding to tubulin, with 79 and 87% inhibition at 1 and 5 µM which comparable active as CA-4 (86 and 97% inhibition at 1 µM and 5 µM respectively). These results indicate that compound 8c exhibits tubulin polymerization inhibition and could compete with the colchicine binding site.

TABLE 2

Inhibition of Tubulin Polymerization and Colchicine Binding by quinoline compounds and CA-4

| Compound | Tubulin assembly[a] IC$_{50}$ ± SD (µM) | Colchicine binding[b] % ± SD | |
|---|---|---|---|
| | | 1 µM drug | 5 µM drug |
| 8a | 13.98 | nd | nd |
| 8c | 1.21 | 79 ± 2 | 87 ± 1 |
| 8e | 2.26 | nd | nd |
| 8g | 8.23 | nd | nd |
| 9c | 20.29 | nd | nd |
| 9e | 1.48 | nd | nd |
| CA-4 | 2.17 | 86 ± 0.9 | 97 ± 2 |

Figure 2A:
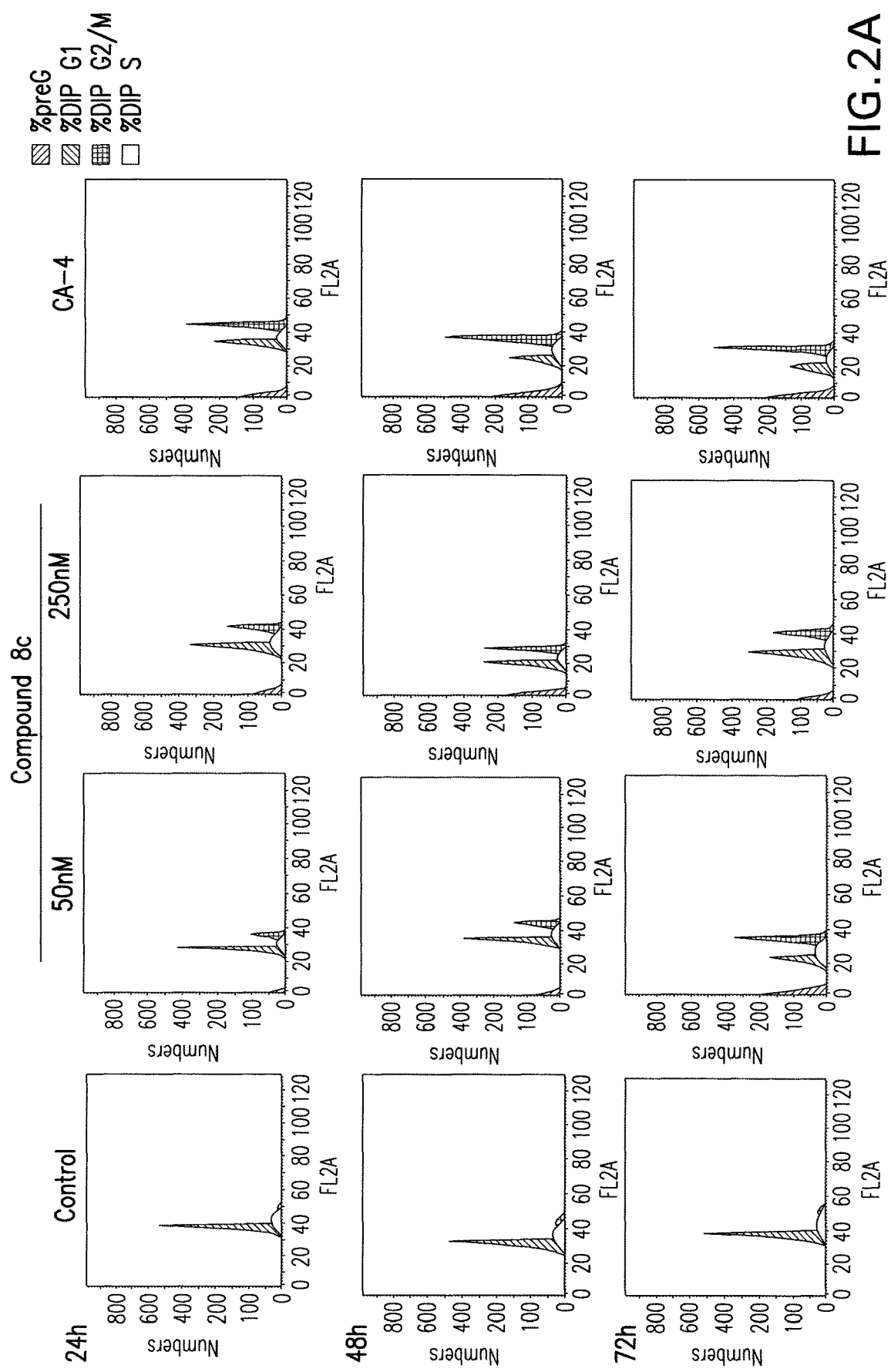
FIGS. 2A-2D show the effect of compound 8c on the cell cycle and apoptosis in MCF-7 cells. (A) Cells were treated with either vehicle [0.1% ethanol (v/v)], CA-4 (50 nM), 8c (50 nM and 250 nM) for 24 h, 48 h and 72 h. Cells were then fixed, stained with PI, and analyzed by flow cytometry. Cell cycle analysis was performed on histograms of gated counts per DNA area (FL2-A). The number of cells with (B) 4N ($G_2$/M), (C) 2N($G_0G_1$), and (D)<2N (sub-$G_1$). DNA content was determined with CellQuest software. Values represent the mean±SEM for three independent experiments. Statistical analysis was performed using two-way ANOVA (*, p<0.05; , p<0.01; *, p<0.001).
Figure 2B:
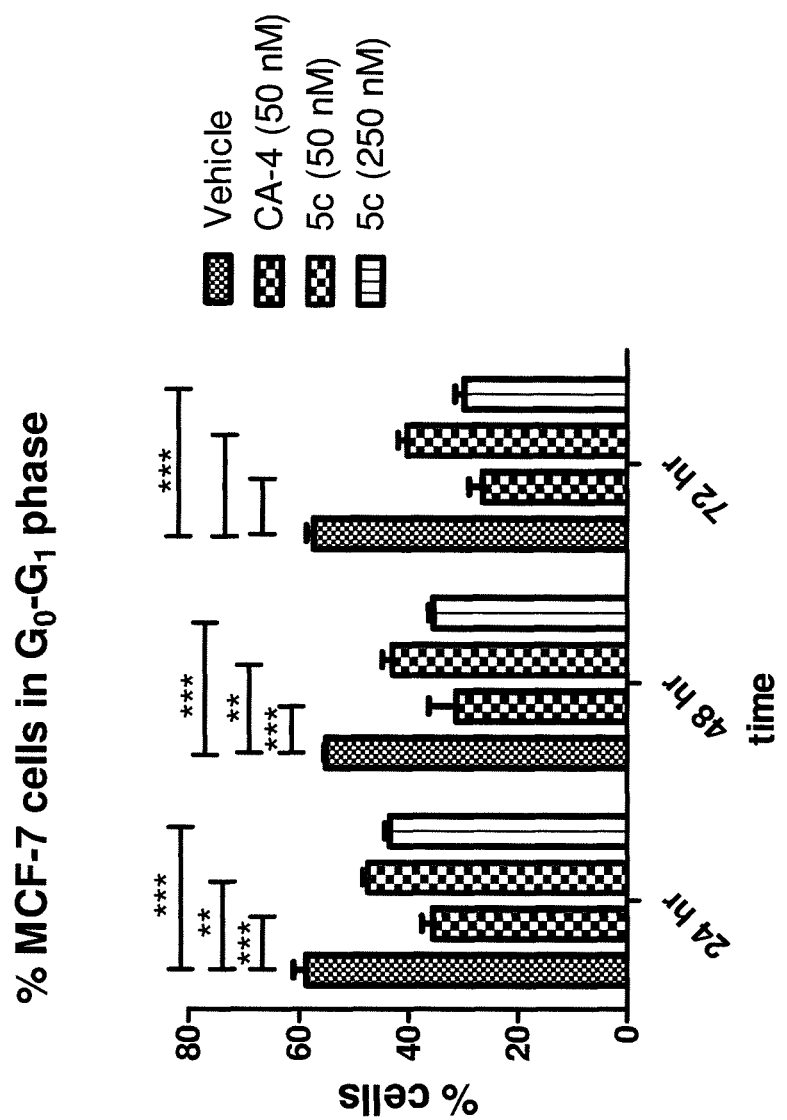
Figure 2C:
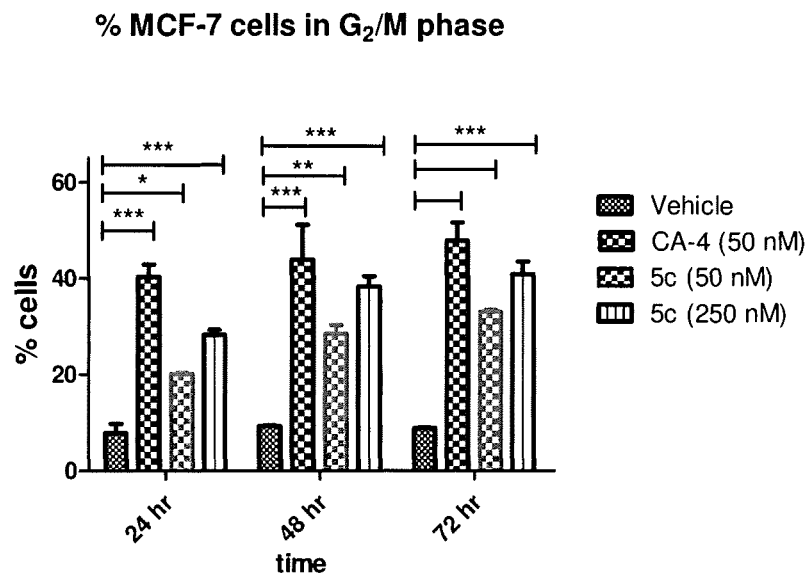
Figure 2D:
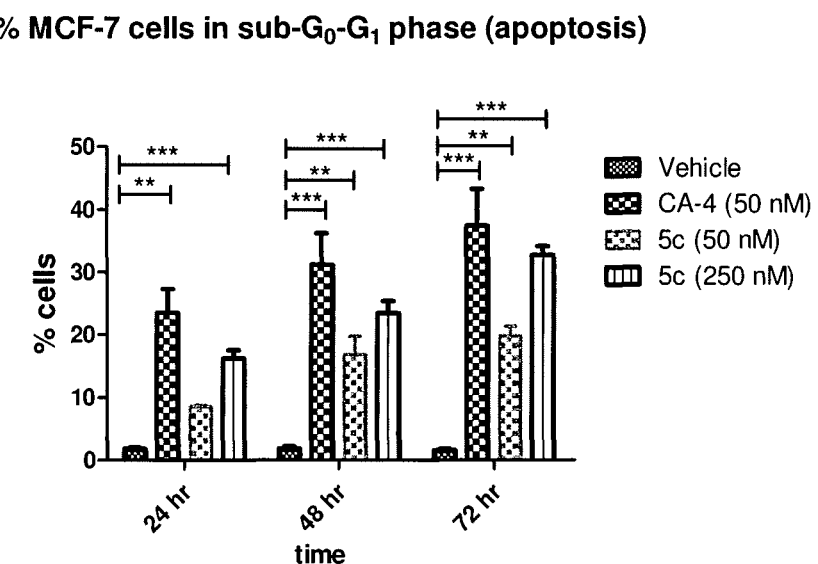

[a]Inhibition of tubulin polymerization. Tubulin was at 10 µM
[b]Inhibition of [$^3$H] colchicine binding. Tubulin and colchicine were at 1 and 5 µM concentrations, respectively Generally, G$_2$/M cell cycle arrest is strongly associated with tubulin polymerization inhibition and is well established that CA-4 causes cell cycle arrest at G$_2$M phase [36-38]. The excellent potency of compound 8c with respect to inhibit MCF-7 cell proliferation prompted us to determine whether the cytotoxicity induced by compound 8c was due to cell cycle arrest. The effect of oxazolone analogue 8c was investigated in breast cancer MCF-7 cells by flow cytometry at two concentrations 50 nM and 250 nM for different time times (0, 24, 48 and 72 h). As shown in FIG. 2A, it was clearly demonstrated that 8c caused a significant G$_2$/M arrest and apoptosis in a time and concentration dependent manner. The percentage of cells in G$_2$/M phase after 48 h was 28.4 and 38.3% at a concentration of 50 nM and 250 nM respectively compared to the control (9.2%) (FIG. 2B). Moreover, there was an increase in the number of cells in G$_2$/M phase after 72 h with 33.0 and 40.8% at a concentration of 50 nM and 250 nM, respectively with a concomitant decrease of cells in G$_0$/G$_1$ phase with 40.3 and 29.8% at a concentration of 50 nM and 250 nM, respectively compared to the control (57.3%). This finding is comparable with CA-4 (50 nM) which caused a significant increase in the percentage of cells in G$_2$/M arrest at 24, 48 and 72 h with 40.3, 43.8 and 47.7% of MCF-7 cells respectively with a concomitant decrease of cells in the cell cycle G0 phase (FIG. 2B,C). 8c was induced a gradual increase in apoptosis as the population in the sub-G1 phase was increased at 24, 48 and 72 h time point with 16.2, 23.4 and 32.7% respectively at a 250 nM compared to 1.5% for untreated cells. Similar results were obtained for CA-4 with 23.5, 31.1 and 37.4% at 24, 48 and 72 h time point, respectively (FIG. 2C). These findings are in agreement with the previously observed for antimitotic derivatives in the series of related quinoline analogues which significantly induce apoptosis and G$_2$M cycle arrest in MCF-7 cells [22, 39-42]

Figure 3A:
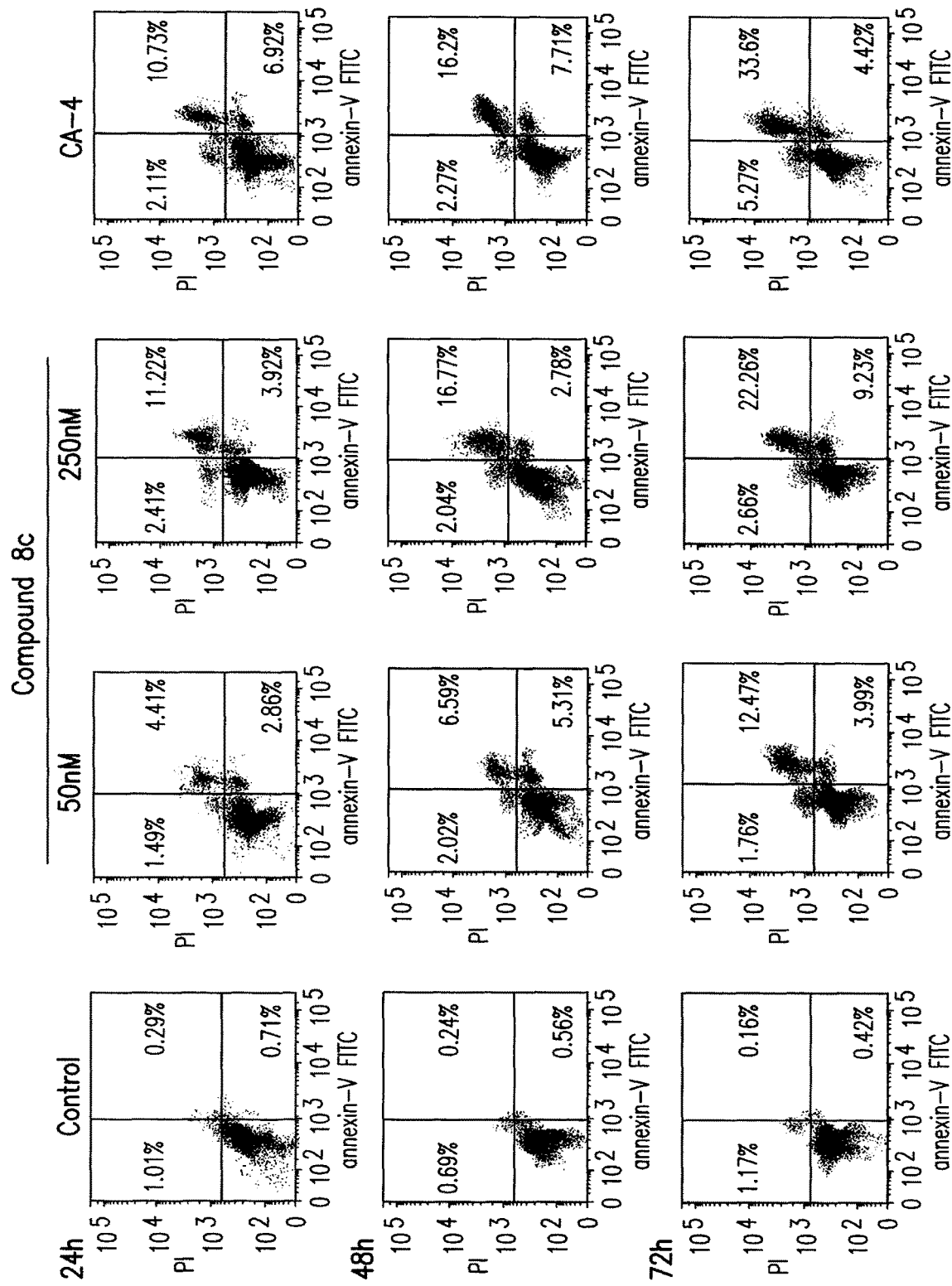
FIGS. 3A-D are test results with compound 8c.
Figure 3B:
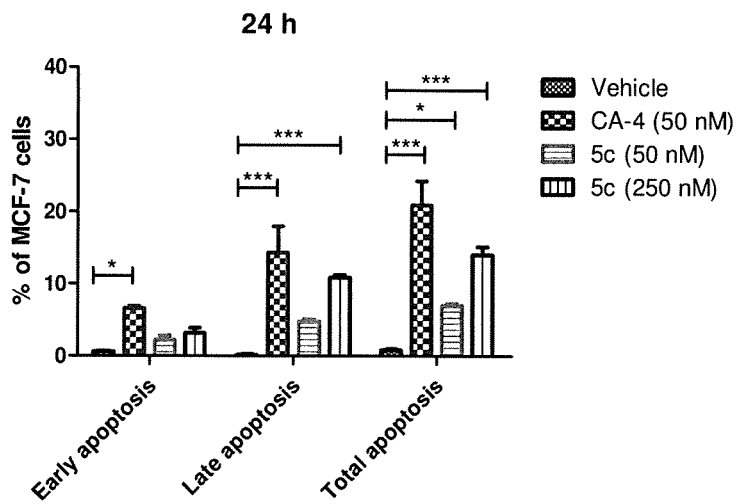
Figure 3C:
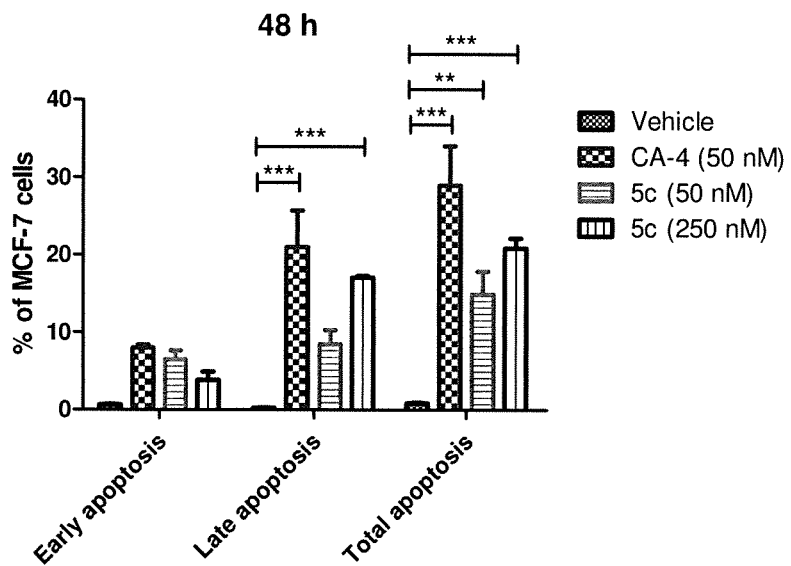
Figure 3D:
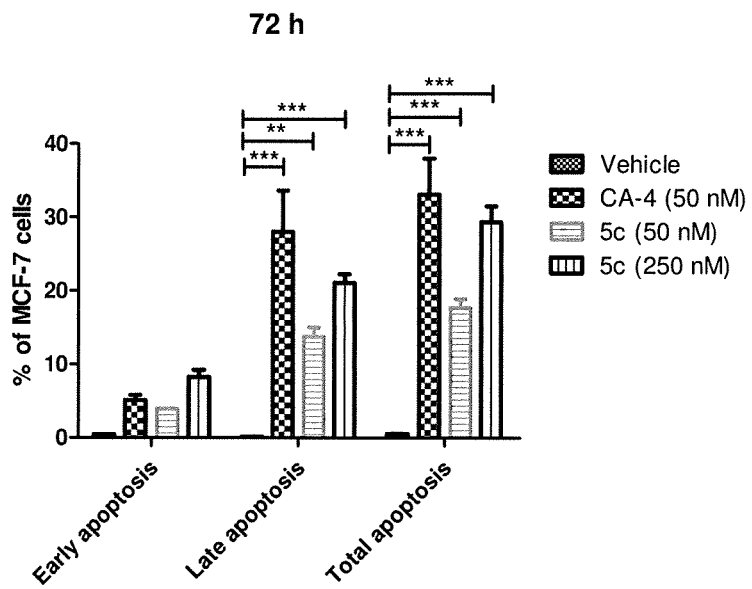

To evaluate the mode of cell death induced by 8c, Annexine-V/PI assay was used. MCF-7 cells were treated with four different concentrations (0, 50 and 250 nM) of compound 8c for at different time points (24, 48 and 72 h). Compound 8c caused a significant accumulation of annexine-V positive cells induced both early and late apoptosis in a concentration and time dependent manner as compared to the untreated control cells. As shown in FIG. 3A, when the cells were treated with 8c at 50 and 250 nM and CA-4 (50 nM) for 48 h time point, the average proportion of Annexin V-staining positive cells (total apoptotic cells) significantly increased from 1% in control cells to 15%, 21% and 29% respectively. The percentage of early and late apoptotic cells together of 8c were increased after 72 h to 17.6% and 29.3% at 50 and 250 nM respectively when compared to the control cells (2%). As supported from cell cycle arrest and apoptosis findings above (FIG. 3B), these results suggested that compound 8c could efficiently induce apoptosis of MCF-7 cells in a dose and time dependent manner.

Figure 4A:
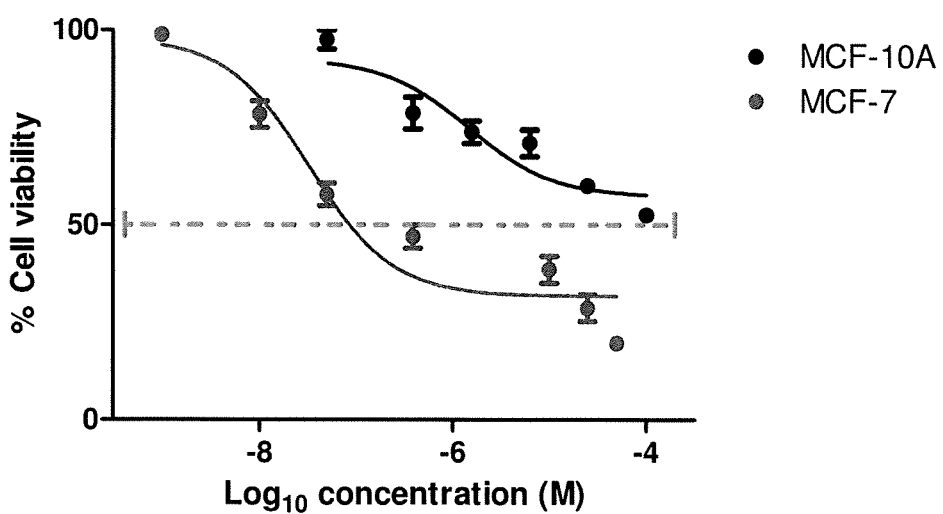
FIGS. 4A and 4B respectively show dose response curves for Compound 8c (FIG. 4A) and CA-4 (FIG. 4B) on the proliferation of breast cancer MCF-7 and normal breast MCF-10A cells. Cells were grown in 96-well plates and treated with serial concentrations of compound 8c or CA-4 for 72 h. Cell viability was expressed as percentage of vehicle control [ethanol 1% (v/v)] treated cells and was measured by MTT assay (average of three independent experiments).
Figure 4B:
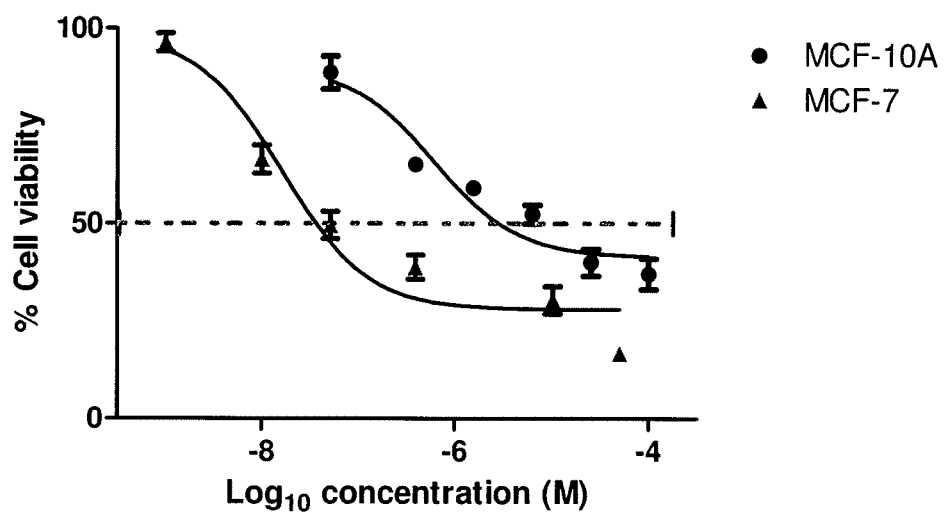

Non-tumourigenic cell line MCF10A (normal epithelial breast) was chosen to investigate the toxicity and selectivity of 8c towards normal cells. As shown in FIG. 4A, the IC$_{50}$ value of 8c was more than 50 µM in MCF-10A cells which was significantly higher than that observed against the MCF-7, HL-60, HCT-116 and HeLa cancer cell lines (IC$_{50}$=19.1, 10.7, 22.5 and 42.7 nM, respectively), Remarkably, 8c was found to be less toxic in normal MCF10A (IC$_{50}$=>50 µM) compared to CA-4 (IC$_{50}$=6.1 µM) (FIG. 4B). These results demonstrated that 8c was less toxic to human normal cells than cancer cells, providing a window of selectivity.

Figure 5A:
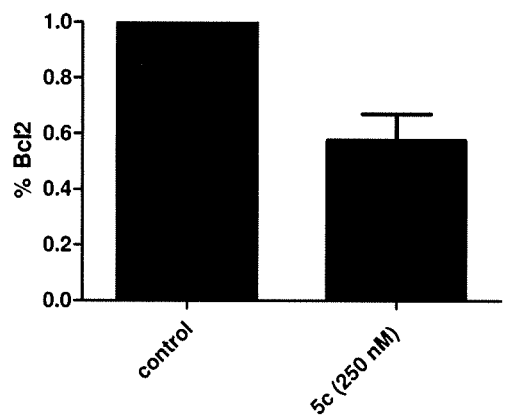
FIGS. 5A-5C respectively show the effect of compound 8c on the expression of anti-apoptotic protein Bcl2 (FIG. 5A), pro-apoptotic protein BAX (FIG. 5B), and Caspase 9 (FIG. 5C) in MCF-7 cells.
Figure 5B:
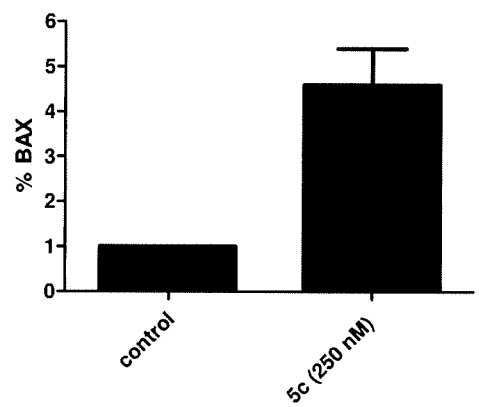

Compound 8c was an effective inducer of mitotic arrest in MCF-7 cells. To further investigate the effects of the novel compound 8c on apoptotic pathway proteins that might have been activated by 8c in MCF-7 cells, the effects of treatment with compound 8c (methyl substituent in quinoline ring) on the expression of intrinsic apoptosis pathway markers, members of Bcl-2 family including the pro-apoptotic protein Bax and anti-apoptotic protein Bcl-2 was examined. MCF-7 cells treated with 8c (250 nM) at 48 h showed a decrease in the expression level of the anti-apoptotic protein Bcl-2 and correspondingly an up-regulation in the expression of the pro-apoptotic protein Bax, FIG. 5A,B.

Figure 5C:
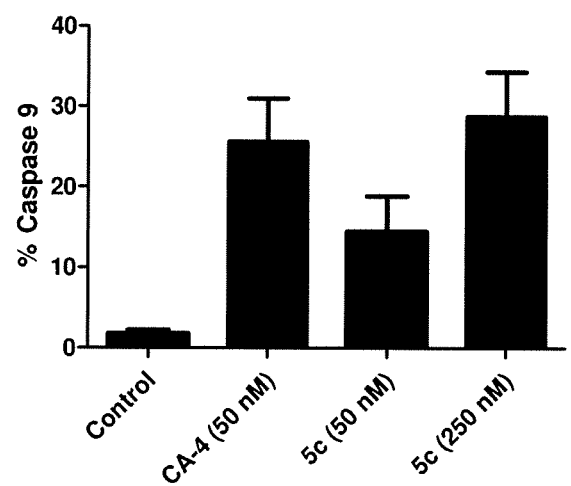

It is well known that activation of caspases plays an essential role apoptosis induction. Particularly, Caspase-9 is one of the important effector caspases that is essential for cell morphological changes associated with the execution of programmed cell death activated by CA-4 treatment [36, 43, 44]. The amount of activated caspase-9 was investigated following MCF-7 cells treated with 8c and CA-4 was used as a positive reference. As illustrated in FIG. 5C, compound 8c at 50 and 250 nM produced about 6 and 16 fold increases in caspase-9 expression respectively. This result confirmed that compound 8c could correlate its cytotoxic activity with the induction of apoptosis through activation of caspase-9.

Figure 6A:
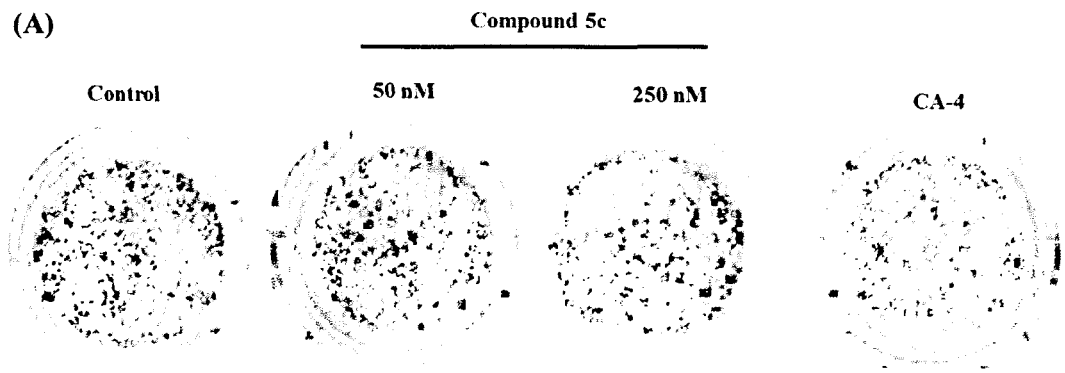
FIG. 6A represents the inhibition of colony formation in MCF-7 cells by 50 and 250 nM of compound 8c and 50 nM of CA-4 for 48 h.
Figure 6B:
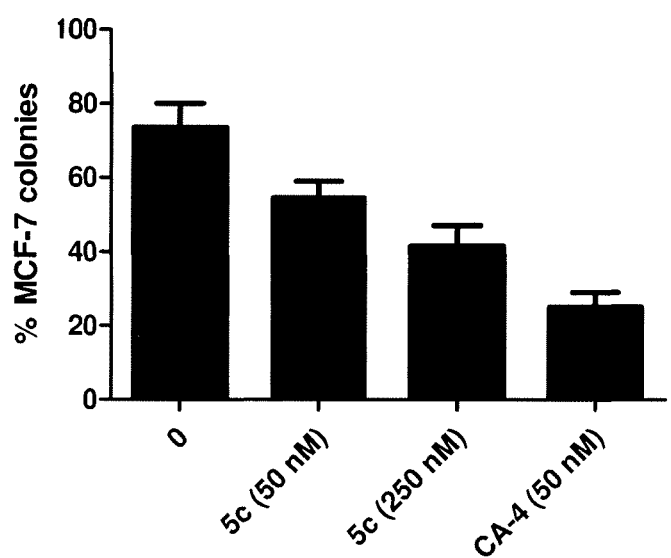
FIG. 6B shows the quantitative analysis of colony formation.

The colony formation assay in MCF-7 was performed to better evaluate the antiproliferative activity of compound 8c. The results are presented in FIG. 6. Compound 8c inhibited the colony formation in a dose dependent manner and the colony formation treated with 8c was inhibited better than that with CA-4

Figure 7A:
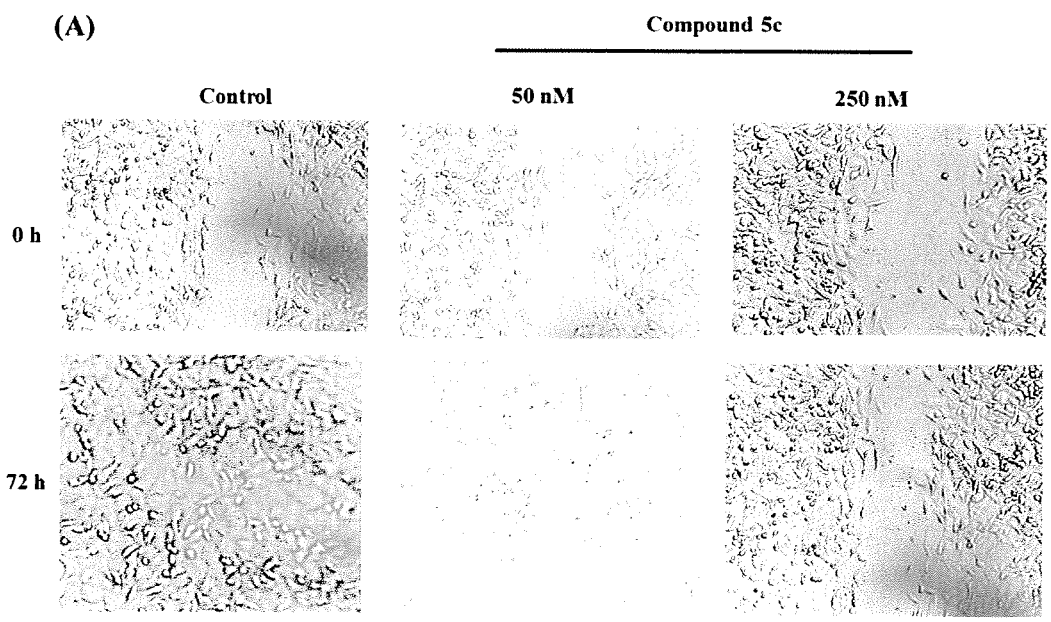
FIG. 7A shows the inhibition of the migration of MCF-7 cells treated with compound 8c for 48 h in the wound healing assay.
Figure 7B:
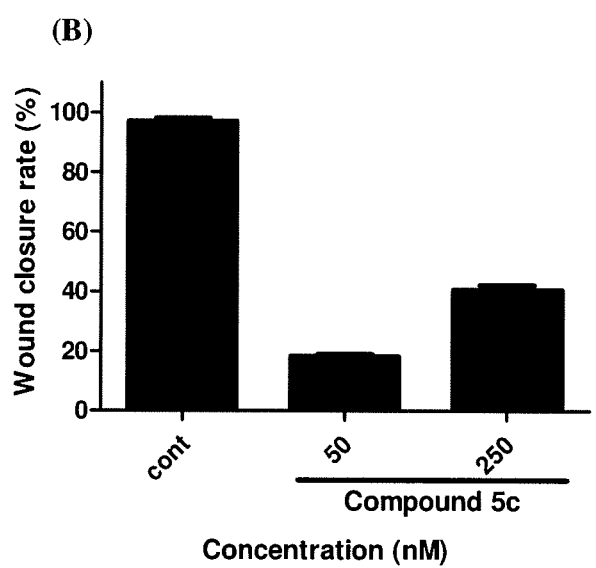
FIG. 7B shows the quantitative analysis of wound closure rate and was calculated as mean±SEM for three independent experiments.

Migration of cancer cells is considered as a critical key in the tumor progression and metastatic cascade [45, 46]. So, compound 8c was evaluated for cell migration by wound healing assay on MCF-7 cell line. In order to investigate the anti-migration activity of compound 8c, the MCF-7 cell culture assay was performed. As illustrated in FIG. 7A after 24 h, the untreated cells migrated to the area that has been initially scraped while the compound 8c treated cells incurred migration inhibition in a dose dependent manner indicating that compound 8c could effectively inhibited cell migration. The significant difference in the wound area shown by 8c with respect to control was demonstrated in FIG. 7B.

Figure 8B:
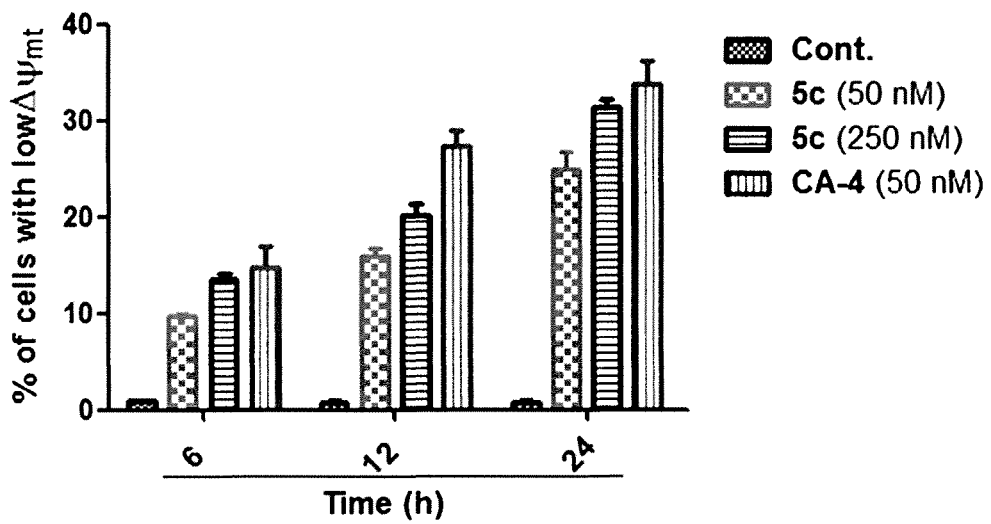
FIG. 8B shows results where cells were then analyzed by flow cytometry as described in the experimental section. Data are presented as mean±SEM of three independent experiments.

It is well established that, mitochondria play a crucial event in the propagation of apoptosis and more specifically the decrease of mitochondrial membrane potential (MMP) is characteristic at the early stage of apoptosis [7, 47-49]. To confirm whether compound 8c could decrease the MMP of MCF-7 cancer cells, MMP was monitored by the fluorescence of the dye DiOC2(3). MCF-7 cells treated with compound 8c (50, 250 nM) showed a concentration and time-dependant increase in the percentage of cells with low $\Delta\psi_{mt}$. As shown in FIG. 8A, the depolarization of the mitochondrial membrane is associated with the appearance of annexin-V positively in the MCF-7 treated cells when they are in an early apoptotic stage, paralleling the results obtained with the annexin-V apoptotic assay. MCF-7 treated with 8c exhibited a marked increase in the percentage of cells with collapsed MMP at 24 h increased from 1.1% to 24.9 and 31.3% at 50 and 250 nM, respectively (FIG. 8B), indicated that compound 8c induce mitochondrial dysfunction which eventually triggered apoptotic cell death. These results are in excellent agreement with other antimitotic CA-4 analogues cause apoptosis following the mitochondrial pathway [50-52].

Figure 9:
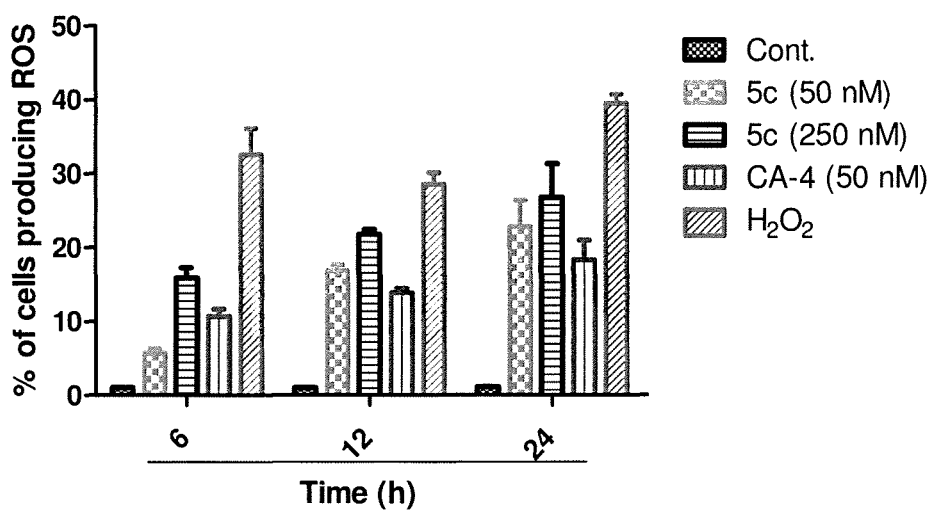
FIG. 9 shows the effect of compound 8c at different time points on ROS production in MCF-7 cells. MCF-7 cells treated without and with 50 and 250 nM of compound 8c and 50 nM of CA-4 and 100 μM $H_2O_2$ for 6 h, 12 h and 24 h. Cells were incubated with DCFDA (25 μM) dye for 1 h at 37° C. in dark. Fluorescence intensity per cell at 525 nm was calculated as mean±SEM for three independent experiments.

The dissipation of mitochondrial potential is associated with mitochondrial production of reactive oxygen species (ROS) [7, 50]. We also evaluated whether ROS production increased after treatment with 8c (50 and 250 nM) and CA-4 (50 nM) as well as Hydrogen peroxide $H_2O_2$ as a positive control. The dye 2,7-dichlorofluorescin diacetate ($H_2$-DCFDA) was used which is oxidized to the fluorescent compound dichlorofluorescein (DCF) upon ROS induction. As shown in FIG. 9, after 24 h compound 8c induced ROS generation with 22.7 and 26.6% at 50 and 250 nM, respectively in comparison with untreated MCF-7 cells (1.0%) and interestingly higher than that of CA-4 (18.3%). These results are revealed that compound 8c induced apoptosis via mitochondrial pathway.

EXAMPLES

The following examples, including experiments and results achieved, are provided for illustrative purposes only and are not to be construed as limiting the present invention. Where chemical structures depict atoms having an unfilled valency, it is to be understood that the valency is satisfied with one or more hydrogen atoms.

Melting points were determined with a Gallenkamp (London, U.K.) melting point apparatus and are uncorrected. IR spectra (KBr, cm$^{-1}$) were recorded on Bruker Vector, 22FT-IR [Fourier Transform Infrared (FTIR), Germany] spectrometer. Unless otherwise specified, proton ($^1$H) and carbon ($^{13}$C) NMR spectra were recorded at room temperature in base filtered CDCl$_3$ on a spectrometer operating at 400 & 300 MHz for proton and 100 &75 MHz for carbon nuclei. The signal due to residual CHCl$_3$ appearing at δ H 7.26 and (CH$_3$)$_2$SO appearing at δ H 2.5 and the central resonance of the CDCl$_3$ "triplet" appearing at δ C 77.0 and for (CD$_3$)$_2$SO "multiplet" appearing at δ C 39.0 were used to reference $^1$H and $^{13}$C NMR spectra, respectively. $^1$H NMR data are recorded as follows: chemical shift (δ) [multiplicity, coupling constant(s) J (Hz), relative integral] where multiplicity is defined as s=singlet; d=doublet; t=triplet; q=quartet; and m=multiplet or combinations of the above. Elemental analyses were determined using Manual Elemental Analyzer Heraeus (Germany) and Automatic Elemental Analyzer CHN Model 2400 Perkin Elmer (USA) at Microanalytical Centre, Faculty of Science, Cairo University, Egypt. All the results of elemental analyses corresponded to the calculated values within experimental error. Progress of the reaction was monitored by thin-layer chromatography (TLC) using precoated TLC sheets with Ultraviolet (UV) fluorescent silica gel (Merck 60F254) and spots were visualized by iodine vapours or irradiation with UV light (254 nm). All the chemicals were purchased from Sigma-Aldrich or Lancaster Synthesis Corporation (U.K.). Intermediates 2-4a-i were prepared according to the reported procedure.[32]

All biochemical assays were performed in triplicate on at least three independent occasions for the determination of mean values reported.

Example 1. General Procedure for Preparation of Oxazolones of Formula IV

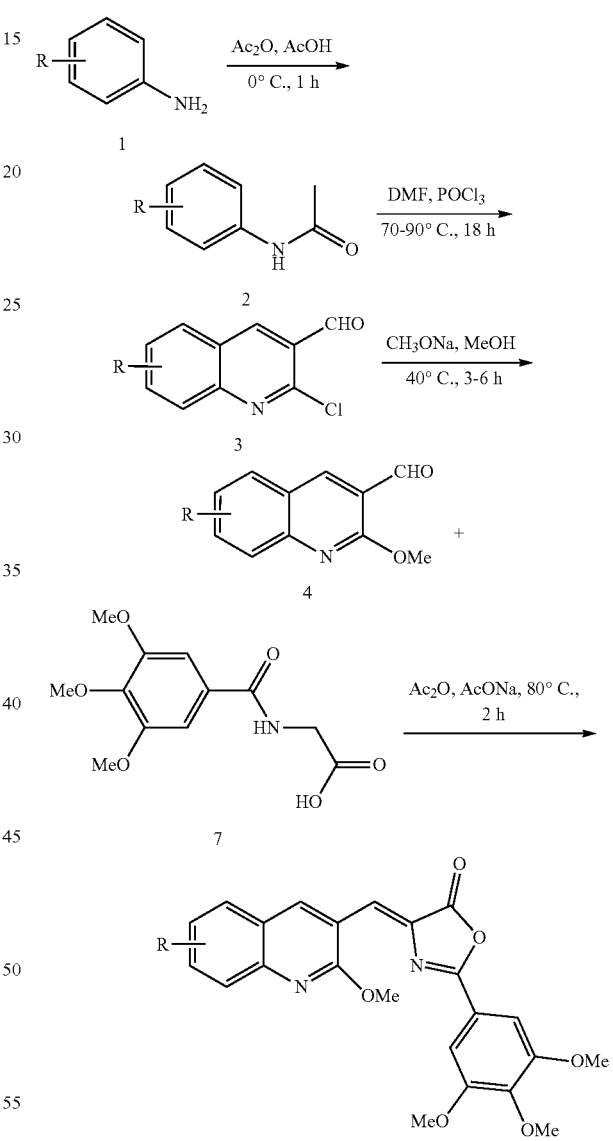

Formula IV

A mixture of N-(3,4,5-trimethoxybenzoyl)glycine 7 (0.30 g, 1.10 mmol) and the appropriate aldehydes 4a-h (1.00 mmol) in acetic anhydride (1 mL) and fused sodium acetate (0.1 g, 1.2 mmol) was heated on an oil bath at 80° C. for 2 h. After cooling down at room temperature the mixture was allowed to stand for 24 h at 0° C. The precipitate was filtered off and washed three times with ice-cooled ethanol (10 mL). The product was crystallized from ethanol.

Example Compounds

4-[(2-Methoxyquinolin-3-yl)methylene]-2-(3,4,5-trimethoxyphenyl)oxazol-5(4H)-one (8a)

Yellow solid, Yield (81%); m.p. 215-217° C. IR (KBr): ν=1776 (C=O), 1621 (C=N), 1599 (C=C) cm$^{-1}$. $^1$H NMR (400 MHz, CDCl$_3$) δ: 9.48 (s, 1H, Ar—H), 7.86-7.81 (m, 2H, Ar—H), 7.71-7.67 (m, 2H, Ar—H), 7.45-7.41 (m, 3H, Ar—H), 4.15 (s, 3H, OCH$_3$), 4.00 (s, 9H, 3OCH$_3$) ppm. $^{13}$C NMR (100 MHz, CDCl$_3$) δ: 167.1, 163.9, 160.0, 153.5, 147.1, 143.1, 142.4, 134.6, 131.5, 128.9, 127.1, 125.2, 124.7, 123.6, 120.1, 118.5, 105.8, 81.1, 56.4, 54.1 ppm. MS (70 eV): m/z (%): 420 (7.79) [M$^+$]; Anal. Calcd for C$_{23}$H$_{20}$N$_2$O$_6$: C, 65.71; H, 4.80; N, 6.66. Found: C, 65.64; H, 4.74; N, 6.71

4-[(2-Methoxy-6-methylquinolin-3-yl)methylene]-2-(3,4,5-trimethoxyphenyl)oxazol-5(4H)-one (8b)

Pale yellow solid, Yield (79%); m.p. 218-220° C. $^1$H NMR (400 MHz, CDCl$_3$) δ: 9.36 (s, 1H, Ar—H), 7.72 (t, J=4 Hz, 2H, Ar—H), 7.56 (s, 1H, Ar—H), 7.49 (d, J=8.5 Hz, 1H, Ar—H), 7.41 (s, 2H, Ar—H), 4.11 (s, 3H, OCH$_3$), 3.98 (d, J=8.0 Hz, 9H, 3OCH$_3$) and 2.51 (s, 3H, CH$_3$) ppm. $^{13}$C NMR (100 MHz, CDCl$_3$) δ: 167.2, 163.8, 159.7, 153.5, 145.7, 143.1, 141.8, 134.4, 134.3, 133.6, 127.8, 126.9, 125.1, 124.1, 120.3, 118.1, 110.0, 105.7, 61.1, 56.4, 53.9, 21.3 ppm. MS (70 eV): m/z (%): 434 (9.79) [M$^+$]; Anal. Calcd for C$_{24}$H$_{22}$N$_2$O$_6$: C, 66.35; H, 5.10; N, 6.45. Found: C, 66.29; H, 5.04; N, 6.50.

4-[(2-Methoxy-7-methylquinolin-3-yl)methylene]-2-(3,4,5-trimethoxyphenyl)oxazol-5(4H)-one (8c)

Yellow solid, Yield (84%); m.p. 233-235° C. $^1$H NMR (400 MHz, CDCl$_3$) δ: 9.50 (s, 1H, Ar—H), 7.76-7.73 (m, 3H, Ar—H), 7.45 (s, 2H, Ar—H), 7.30-7.28 (m, 1H, Ar—H), 4.20 (s, 3H, OCH$_3$), 4.00 (d, J=8.0 Hz, 9H, 3OCH$_3$), 2.58 (s, 3H, CH$_3$) ppm. $^{13}$C NMR (100 MHz, CDCl$_3$) δ: 167.2, 163.8, 162.6, 160.2, 153.5, 143.1, 142.8, 142.5, 134.3, 128.7, 127.0, 126.3, 123.9, 123.1, 120.2, 117.6, 105.7, 61.1, 56.4, 54.6, 22.1 ppm. MS (70 eV): m/z (%): 434 (6.90) [M$^+$]; Anal. Calcd for C$_{24}$H$_{22}$N$_2$O$_6$: C, 66.35; H, 5.10; N, 6.45. Found: C, 66.32; H, 5.05; N, 6.47.

4-[(2-Methoxy-8-methylquinolin-3-yl)methylene]-2-(3,4,5-trimethoxyphenyl)oxazol-5(4H)-one (8d)

Yellow solid, Yield (82%); m.p. 236-238° C. $^1$H NMR (400 MHz, CDCl$_3$) δ: 9.44 (s, 1H, Ar—H), 7.73 (s, 1H, Ar—H), 7.64 (d, J=8.0 Hz, 1H, Ar—H), 7.52 (d, J=6.40 Hz, 1H, Ar—H), 7.39 (s, 2H, Ar—H), 7.32-7.28 (m, 1H, Ar—H), 4.12 (s, 3H, OCH$_3$), 3.98 (s, 9H, 3OCH$_3$), 2.68 (s, 3H, CH$_3$) ppm. $^{13}$C NMR (100 MHz, CDCl$_3$) δ: 167.2, 163.8, 159.1, 153.7, 146.0, 143.1, 142.7, 135.4, 134.3, 131.6, 126.7, 125.0, 124.3, 124.0, 120.2, 118.0, 105.6, 61.1, 56.3, 53.7, 17.5 ppm. MS (70 eV): m/z (%): 434 (9.50) [M$^+$]; Anal. Calcd for C$_{24}$H$_{22}$N$_2$O$_6$: C, 66.35; H, 5.10; N, 6.45. Found: C, 66.30; H, 5.04; N, 6.51.

4-[2,6-Dimethoxyquinolin-3-yl)methylene]-2-(3,4,5-trimethoxyphenyl)oxazol-5(4H)-one (8e)

Yellow solid, Yield (84%); m.p. 242-244° C. 1784 (C=O), 1618 (C=N), 1586 (C=C) cm$^{-1}$. $^1$H NMR (400 MHz, CDCl$_3$) δ: 9.33 (s, 1H, Ar—H), 7.73 (d, J=8.0 Hz, 2H, Ar—H), 7.42-7.32 (m, 3H, Ar—H), 7.12 (s, 1H, Ar—H), 4.10 (s, 3H, OCH$_3$), 3.99 (s, 9H, 3OCH$_3$) 3.93 (s, 3H, OCH$_3$) ppm. $^{13}$C NMR (100 MHz, CDCl$_3$) δ: 167.1, 163.8, 158.9, 156.4, 153.5, 143.2, 143.0, 141.1, 134.5, 128.5, 125.7, 124.2, 123.0, 120.2, 118.4, 107.4, 105.9, 61.2, 56.5, 55.6, 53.8 ppm. MS (70 eV): m/z (%): 450 (8.40) [M$^+$]; Anal. Calcd for C24H22N$_2$O$_7$: C, 64.00; H, 4.92; N, 6.22. Found: C, 63.94; H, 4.87; N, 6.28.

4-[(2,7-Dimethoxyquinolin-3-yl)methylene]-2-(3,4,5-trimethoxyphenyl)oxazol-5(4H)-one (8f)

Yellow solid, Yield (84%); m.p. 221-223° C. $^1$H NMR (400 MHz, CDCl$_3$) δ: 9.39 (s, 1H, Ar—H), 7.70-7.66 (m, 2H, Ar—H), 7.38 (s, 2H, Ar—H), 7.16 (s, 1H, Ar—H), 7.04 (d, J=8.0 Hz, 1H, Ar—H), 4.11 (s, 3H, OCH$_3$), 3.97 (s, 9H, 3OCH$_3$) 3.95 (s, 3H, OCH$_3$) ppm. $^{13}$C NMR (100 MHz, CDCl$_3$) δ: 167.4, 163.3, 162.8, 160.7, 153.5, 149.7, 142.8, 142.0, 133.3, 130.2, 124.4, 120.4, 120.1, 117.2, 115.9, 106.4, 105.5, 61.2, 56.2, 55.6, 53.9 ppm. MS (70 eV): m/z (%): 450 (7.30) [M$^+$]; Anal. Calcd for C$_{24}$H$_{22}$N$_2$O$_7$: C, 64.00; H, 4.92; N, 6.22. Found: C, 63.96; H, 4.96; N, 6.25.

4-[(7-Isopropoxy-2-methoxyquinolin-3-yl)methylene]-2-(3,4,5-trimethoxyphenyl)oxazol-5(4H)-one (8g)

Yellow solid, Yield (77%); m.p. 227-229° C. $^1$H NMR (400 MHz, CDCl$_3$) δ ppm: 9.41 (s, 1H, Ar—H), 7.74-7.67 (m, 2H, Ar—H), 7.41 (s, 2H, Ar—H), 7.16-7.00 (m, 2H, Ar—H), 4.87-4.76 (m, 1H, OCH—), 4.12 (s, 3H, OCH$_3$), 3.98 (s, 9H, 3OCH$_3$), 1.45 (d, J=4.0 Hz, 6H, 2 CH$_3$) ppm. $^{13}$C NMR (100 MHz, CDCl$_3$) δ: 167.4, 163.1, 161.2, 160.7, 153.5, 149.5, 142.9, 141.9, 133.2, 130.3, 124.6, 120.4, 119.9, 118.2, 115.7, 107.9, 105.5, 70.3, 61.3, 56.4, 53.9, 22.0 ppm. MS (70 eV): m/z (%): 478 (9.50) [M$^+$]; Anal. Calcd for C$_{26}$H$_{26}$N$_2$O$_7$: C, 65.26; H, 5.48; N, 5.85. Found: C, 65.21; H, 5.45; N, 5.91.

4-[(7-(Benzyloxy)-2-methoxyquinolin-3-yl)methylene]-2-(3,4,5-trimethoxyphenyl)oxazol-5(4H)-one (8h)

Pale yellow solid, Yield (73%); m.p. 247-249° C. $^1$H NMR (400 MHz, CDCl$_3$) δ: 9.43 (s, 1H, Ar—H), 7.72 (t, J=8 Hz, 2H, Ar—H), 7.51-7.35 (m, 6H, Ar—H), 7.28-7.26 (m, 2H, Ar—H), 7.14 (d, 1H, J=8.0 Hz, 1H, Ar—H), 5.21 (s, 2H, OCH$_2$—), 4.12 (s, 3H, OCH$_3$), 3.98 (s, 9H, 3OCH$_3$) ppm. $^{13}$C NMR (100 MHz, CDCl$_3$) δ: 167.4, 163.3, 161.9, 160.8, 153.5, 149.4, 142.9, 141.9, 136.2, 133.5, 130.2, 128.7, 128.3, 127.7, 124.4, 120.4, 120.3, 117.5, 116.0, 107.5, 105.6, 70.3, 61.3, 56.4, 53.9 ppm. MS (70 eV): m/z (%): 526 (7.30) [M$^+$]; Anal. Calcd for C$_{30}$H$_{26}$N$_2$O$_7$: C, 68.43; H, 4.98; N, 5.35. Found: C, 68.39; H, 4.92; N, 5.41.

Example 2. General Procedure for Preparation of Imidazoles of Formula V

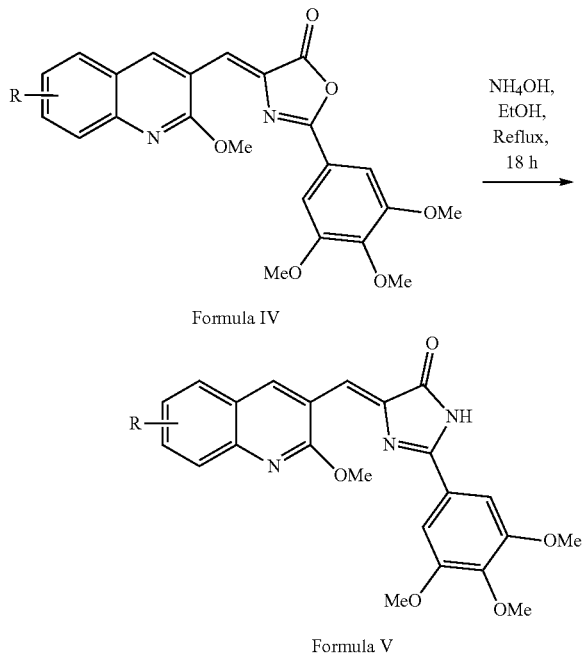

The appropriate oxazolones 8a-h (1 mmol) was stirred and heated under reflux in ethanol (10 mL) containing ammonium hydroxide (10 mL) then the reaction was monitored by TLC. After 24 h the reaction was completed, the solvent was concentrated then cooled, the precipitated was filtered off and crystallized from ethanol.

Example Compounds

5-[(2-Methoxyquinolin-3-yl)methylene]-2-(3,4,5-trimethoxyphenyl)-3,5-dihydro-4H-imidazol-4-one (9a)

Yellow solid, Yield (81%); m.p. 230-232° C. IR (KBr): ν=3222 (NH), 1709 (C=O), 1642 (C=N), 1615, 1589 (C=C) cm$^{-1}$. $^1$H NMR (400 MHz, DMSO-d$_6$) δ: 12.22 (s, 1H, exch., NH), 9.69 (s, 1H, Ar—H), 8.03 (d, J=8.0 Hz, 1H, Ar—H), 7.80-7.70 (m, 2H, Ar—H), 7.59 (s, 2H, Ar—H), 7.49 (t, J=8.0 Hz, 1H, Ar—H), 7.28 (s, 1H, Ar—H), 4.11 (s, 3H, OCH$_3$), 3.94 (s, 6H, 2OCH$_3$), 3.80 (s, 3H, OCH$_3$) ppm. $^{13}$C NMR (100 MHz, DMSO-d$_6$) δ: 172.4, 169.7, 165.2, 162.5, 160.1, 153.8, 146.2, 142.7, 141.9, 131.6, 129.5, 127.0, 125.5, 125.3, 123.3, 115.9, 105.8, 61.0, 56.6, 54.4 ppm. MS (70 eV): m/z (%): 419 (5.40) [M$^+$]; Anal. Calcd for C$_{23}$H$_{21}$N$_3$O$_5$: C, 65.86; H, 5.05; N, 10.02. Found: C, 65.81; H, 4.99; N, 10.09.

5-[(2-Methoxy-6-methylquinolin-3-yl)methylene]-2-(3,4,5-trimethoxyphenyl)-3,5-dihydro-4H-imidazol-4-one (9b)

Yellow solid, Yield (81%); m.p. 223-225° C. $^1$HNMR (400 MHz, DMSO-d$_6$) δ: 12.18 (s, 1H, exch., NH), 9.55 (s, 1H, Ar—H), 7.74-7.54 (m, 5H, Ar—H), 7.25 (d, J=6.6 Hz, 1H, Ar—H), 4.07 (s, 3H, OCH$_3$), 3.93 (s, 6H, OCH$_3$), 3.80 (s, 3H, OCH$_3$), 2.47 (s, 3H, CH$_3$) ppm. $^{13}$C NMR (100 MHz, DMSO-d$_6$) δ: 172.0, 162.2, 156.0, 153.7, 144.6, 142.6, 142.4, 141.2, 134.4, 133.4, 128.1, 126.8, 125.4, 123.2, 119.3, 116.2, 110.0, 106.2, 60.7, 56.8, 54.2, 21.3 ppm. MS (70 eV): m/z (%): 433 (5.60) [M$^+$]; Anal. Calcd for C$_{24}$H$_{23}$N$_3$O$_5$: C, 66.50; H, 5.35; N, 9.69. Found: C, 66.41; H, 5.28; N, 9.75.

5-[(2-Methoxy-7-methylquinolin-3-yl)methylene]-2-(3,4,5-trimethoxyphenyl)-3,5-dihydro-4H-imidazol-4-one (9c)

Yellow solid, Yield (84%); m.p. 236-238° C. IR (KBr): ν=3215 (NH), 1711 (C=O), 1639 (C=N), 1590 (C=C) cm$^{-1}$. $^1$H NMR (400 MHz, DMSO-d$_6$) δ: 12.17 (s, 1H, exch. NH), 9.63 (s, 1H, Ar—H), 7.92 (d, J=8.0 Hz, 1H, Ar—H), 7.58 (s, 3H, Ar—H), 7.32 (d, J=8 Hz, 1H, Ar—H), 7.27 (s, 1H, Ar—H), 4.09 (s, 3H, OCH$_3$), 3.94 (s, 6H, 2OCH$_3$), 3.80 (s, 3H, OCH$_3$), 2.53 (s, 3H, CH$_3$) ppm. $^{13}$C NMR (100 MHz, DMSO-d$_6$) δ: 162.6, 162.5, 160.3, 153.9, 142.2, 141.5, 129.1, 127.1, 126.3, 123.6, 118.3, 115.8, 105.6, 60.8, 56.5, 54.2, 22.0 ppm. MS (70 eV): m/z (%): 433 (8.40) [M$^+$]; Anal. Calcd for C$_{24}$H$_{23}$N$_3$O$_5$: C, 66.50; H, 5.35; N, 9.69. Found: C, 66.44; H, 5.32; N, 9.72.

5-[(2-Methoxy-8-methylquinolin-3-yl)methylene]-2-(3,4,5-trimethoxy phenyl)-3,5-dihydro-4H-imidazol-4-one (9d)

Yellow solid, Yield (82%); m.p. 233-235° C. $^1$H NMR (400 MHz, DMSO-d$_6$) δ: 12.16 (s, 1H, exch., NH), 9.59 (s, 1H, Ar—H), 7.80 (s, 1H, Ar—H), 7.70 (d, J=8 Hz, 1H, Ar—H), 7.59-7.56 (m, 3H, Ar—H), 7.29 (s, 1H, Ar—H), 4.10 (s, 3H, OCH$_3$), 3.95 (s, 6H, 2OCH$_3$), 3.80 (s, 3H, OCH$_3$), 2.49 (s, 3H, CH$_3$) ppm. $^{13}$C NMR (100 MHz, DMSO-d$_6$) δ: 161.9, 158.2, 153.3, 142.2, 141.6, 141.5, 134.2, 131.3, 126.7, 124.8, 124.5, 118.6, 115.4, 105.3, 60.2, 56.1, 53.5, 17.1 ppm. MS (70 eV): m/z (%): 433 (7.12) [M$^+$]; Anal. Calcd for C$_{24}$H$_{23}$N$_3$O$_5$: C, 66.50; H, 5.35; N, 9.69. Found: C, 66.47; H, 5.30; N, 9.73.

5-[(2,6-Dimethoxyquinolin-3-yl)methylene]-2-(3,4,5-trimethoxyphenyl)-3,5-dihydro-4H-imidazol-4-one (9e)

Yellow solid, Yield (84%); m.p. 253-255° C. $^1$HNMR (400 MHz, DMSO-d$_6$) δ: 12.03 (s, 1H, exchangeable, NH), 9.50 (s, 1H, Ar—H), 7.83-7.77 (m, 1H, Ar—H), 7.53 (s, 2H, Ar—H), 7.48 (s, 1H, Ar—H), 7.20-7.05 (m, 2H, Ar—H), 4.04 (s, 3H, OCH$_3$), 3.90 (s, 9H, 3OCH$_3$), 3.79 (s, 3H, OCH$_3$) ppm. $^{13}$C NMR (100 MHz, DMSO-d$_6$) δ: 164.6, 161.9, 157.1, 156.9, 154.1, 142.8, 141.9, 140.0, 128.4, 125.1, 124.1, 118.9, 110.0, 109.3, 108.0, 105.3, 60.7, 57.0, 56.2, 54.4 ppm. MS (70 eV): m/z (%): 449 (8.35) [M$^+$]; Anal. Calcd for C$_{24}$H$_{23}$N$_3$O$_6$: C, 64.16; H, 5.16; N, 9.35. Found: C, 64.11; H, 5.12; N, 9.31.

5-[(2,7-Dimethoxyquinolin-3-yl)methylene]-2-(3,4,5-trimethoxyphenyl)-3,5-dihydro-4H-imidazol-4-one (9f)

Yellow solid, Yield (86%); m.p. 241-243° C. $^1$HNMR (400 MHz, DMSO-d$_6$) δ: 12.10 (s, 1H, exch., NH), 9.57 (s, 1H, Ar—H), 7.86 (d, J=8.0 Hz, 1H, Ar—H), 7.53 (s, 2H, Ar—H), 7.23 (s, 1H, Ar—H), 7.15-7.08 (m, 2H, Ar—H), 4.07 (s, 3H, OCH$_3$), 3.92 (s, 6H, 2OCH$_3$), 3.79 (s, 3H, OCH$_3$) ppm. $^{13}$C NMR (100 MHz, DMSO-d$_6$) δ: 172.1, 162.4, 160.6, 153.6, 148.4, 141.8, 141.6, 130.8, 123.3, 120.3, 117.3, 116.5, 106.7, 105.6, 60.7, 56.6, 56.0, 54.3 ppm. MS (70 eV): m/z (%): 449 (5.65) [M$^+$]; Anal. Calcd for $C_{24}H_{23}N_3O_6$: C, 64.16; H, 5.16; N, 9.35. Found: C, 64.13; H, 5.10; N, 9.29.

5-((7-Isopropoxy-2-methoxyquinolin-3-yl)methylene)-2-(3,4,5-trimethoxy phenyl)-3,5-dihydro-4H-imidazol-4-one (9g)

Yellow solid, Yield (77%); m.p. 238-240° C. $^1$HNMR (400 MHz, DMSO-$d_6$) δ: 12.19 (s, 1H, exch., NH), 9.61 (s, 1H, Ar—H), 7.92 (d, J=8.0 Hz, 1H, Ar—H), 7.58 (s, 2H, Ar—H), 7.28 (s, 1H, Ar—H), 7.17 (s, 1H, Ar—H), 7.08 (d, J=8.0 Hz, 1H, Ar—H), 4.90-4.83 (m, 1H, OCH), 4.09 (s, 3H, OCH$_3$), 3.94 (s, 6H, 2OCH$_3$), 3.79 (s, 3H, OCH$_3$), 1.37 (s, 3H, CH$_3$) 1.36 (s, 3H, CH$_3$) ppm. $^{13}$C NMR (100 MHz, DMSO-$d_6$) δ: 170.3, 166.5, 166.0, 160.3, 153.7, 148.2, 141.2, 130.9, 120.1, 116.4, 105.7, 69.9, 60.6, 56.5, 54.2, 22.1 ppm. MS (70 eV): m/z (%): 477 (9.25) [M$^+$]; Anal. Calcd for $C_{26}H_{27}N_3O_6$: C, 65.40; H, 5.70; N, 8.80. Found: C, 65.35; H, 5.66; N, 8.86.

5-[(7-(Benzyloxy)-2-methoxyquinolin-3-yl)methylene]-2-(3,4,5-trimethoxy phenyl)-3,5-dihydro-4H-imidazol-4-one (9h)

Yellow solid, Yield (73%); m.p. 259-261° C. $^1$H NMR (400 MHz, DMSO-$d_6$) δ: 12.16 (s, 1H, exch., NH), 9.62 (s, 1H, Ar—H), 7.95 (d, J=8 Hz, 1H, Ar—H), 7.58-7.28 (m, 10H, ArH), 5.30 (s, 2H, OCH$_2$—), 4.09 (s, 3H, OCH$_3$), 3.94 (s, 6H, 2OCH$_3$), 3.79 (s, 3H, OCH$_3$) ppm. $^{13}$C NMR (400 MHz, DMSO-$d_6$) δ: 171.8, 169.1, 161.6, 161.5, 153.6, 148.3, 142.0, 141.7, 137.5, 137.1, 133.5, 130.7, 129.3, 128.7, 128.3, 123.2, 120.4, 118.0, 116.7, 116.5, 108.2, 105.8, 70.6, 60.7, 56.5, 54.4 ppm. MS (70 eV): m/z (%): 525 (6.75) [M$^+$]; Anal. Calcd for $C_{30}H_{27}N_3O_6$: C, 68.56; H, 5.18; N, 8.00. Found: C, 68.51; H, 5.13; N, 8.05.

Example 3. Cell Culture

All the human tumour cell lines MCF-7, HCT-116, HL-60 and HeLa were cultured in Dulbecco's Modified Eagle's Medium (DMEM) with 10% fetal bovine serum, 2 mM L-glutamine and 100 g/mL penicillin/streptomycin. Cells were maintained at 37° C. in 5% C02 in a humidified incubator. All cells were sub-cultured 3 times/week by trypsinization using TrypLE Express (1×).

Example 4. Cell Viability Assay

The quinoline compounds were evaluated for antiproliferative effect using the MTT viability assay of four cancer cell lines (MCF-7, HCT-116, HL-60 and HeLa) and normal breast cells MCF-10A to calculate the relative IC$_{50}$ values for each compound. Cells were seeded in triplicate in 96-well plates at a density of 10×10$^3$ cells/ml in a total volume of 200 μl per well. 0.1% of DMSO was used as a vehicle control. After this time, they were treated with 2 μl test compound which had been pre-prepared as stock solutions in ethanol to furnish the concentration range of study, 1 nM to 50 μM, and re-incubated for a further 72 h. The culture medium was then removed, and the cells washed with 100 μL phosphate buffered saline (PBS) and 50 μL MTT added, to reach a final concentration of 1 mg/mL MTT added. Cells were incubated for 2 h in darkness at 37° C. At this point solubilisation was begun through the addition of 200 mL DMSO and the cells maintained at room temperature in darkness for 20 min to ensure thorough colour diffusion before reading the absorbance. Plates were incubated for 72 hours at 37° C.+5% $CO_2$, The MTT (5 mg/mL in PBS) was added and incubated for another 4 h, the optical density was detected with a microplate reader at 570 nm. Results were expressed as percentage viability relative to vehicle control (100%). Dose response curves were plotted and IC$_{50}$ values (concentration of drug resulting in 50% reduction in cell survival) were obtained using the commercial software package Prism (GraphPad Software, Inc., La Jolla, Calif., USA). All the experiments were repeated in at least three independent experiments.

Example 5. Tubulin Polymerization Assay

The assembly of purified bovine tubulin was monitored using a kit, BK006, purchased from Cytoskeleton Inc., (Denver, Colo., USA). The assay was carried out in accordance with the manufacturer's instructions using the standard assay conditions [53]. Briefly, purified (>99%) bovine brain tubulin (3 mg/mL) in a buffer consisting of 80 mM PIPES (pH 6.9), 0.5 mM EGTA, 2 mM MgCl$_2$, 1 mM GTP and 10% glycerol was incubated at 37° C. in the presence of either vehicle (2% (v/v) ddH$_2$O), CA-4, quinoline compounds. Light is scattered proportionally to the concentration of polymerized microtubules in the assay. Therefore, tubulin assembly was monitored turbidimetrically at 340 nm in a Spectramax 340 PC spectrophotometer (Molecular Devices, Sunnyvale, Calif., USA). The concentration that inhibits tubulin polymerization by 50% (IC$_{50}$) was determined using area under the curve (AUC). The AUC of the untreated controls were considered as 100% polymerization. The IC$_{50}$ value for each compound was computed using GraphPad Prism Software.

Example 6. Colchicine Site Competitive Binding Assay

The affinity of compounds 8c to colchicine binding site was determined using Colchicine Site Competitive Assay kit CytoDYNAMIX Screen15 (Cytoskeleton, Inc., CO, USA) using the standard protocol of the manufacturer to determine Ki values (μM). Biotin-labelled tubulin (0.5 μg) in 10 μL of reaction buffer was mixed with [3H]colchicine (0.08 μM, PerkinElmer, Waltham, Mass.) and the test compounds (positive control colchicine, negative control vinblastine, G-1, fluorescent G-1, or 2-ME) in a 96-well plate (final volume: 100 μL). After incubating for 2 h at 37° C. with gentle shaking, streptavidin-labelled yttrium SPA beads (80 μg in 20 μL reaction buffer, PerkinElmer, Waltham, Mass.) were added to each well and incubated for 30 min at 4° C. The plates were then read on a scintillation counter (Packard Instrument, Topcount Microplate Reader) and the percentage of inhibition was calculated [54]

Example 7. Cell Cycle Analysis

MCF-7 cells were seeded at a density of 1×10$^5$ cells/well in 6-well plates and treated with CA-4 (50 nM) and compound 8c (50 and 250 nM) for 24, 48 and 72 hr. The cells were collected by trypsinization and centrifuged at 800×g for 15 min. Cells were washed twice with ice-cold PBS and fixed in ice-cold 70% ethanol overnight at −20° C. Fixed cells were centrifuged at 800×g for 15 min and stained with 50 μg/mL of PI, containing 50 μg/mL of DNase-free RNase A, at 37° C. for 30 min. The DNA content of cells (10,000 cells/experimental group) was analysed by flow cytometer at 488 nm using a FACSCalibur flow cytometer (BD Biosciences, San Jose, Calif.) and all data were recorded and analyzed using the CellQuest Software (Becton-Dickinson).

Example 8. Annexin V/PI Apoptotic Assay

Apoptotic cell death was detected by flow cytometry using Annexin V and propidium iodide (PI). MCF-7 Cells were seeded in 6 well plated at density of $1 \times 10^5$ cells/mL and treated with vehicle (0.1% (v/v) EtOH), positive control (CA-4) or compound 8c (50 and 250 µM) for 24, 48 and 72 hr. Cells were then harvested and prepared for flow cytometric analysis. Cells were washed in 1× binding buffer (20× binding buffer: 0.1M HEPES, pH 7.4; 1.4 M NaCl; 25 mM $CaCl_2$) diluted in $dH_2O$) and incubated in the dark for 30 minutes on ice in Annexin V-containing binding buffer [1:100]. Cells were then washed once in binding buffer and then re-suspended in PI-containing binding buffer [1:1000]. Samples were analysed immediately using the BD accuri flow cytometer and prism software for analysis the data. Four populations are produced during the assay Annexin V and PI negative (Q4, healthy cells), Annexin V positive and PI negative (Q3, early apoptosis), Annexin V and PI positive (Q2, late apoptosis) and Annexin V negative and PI positive (Q1, necrosis).

Example 9. Evaluation of Expression Levels of Anti-Apoptotic Proteins Bcl-2, Pro-Apoptotic Proteins Bax and Caspase 9

Bcl-2 content of MCF-7 cells was assessed by ELISA Kit purchased Zymed laboratories, invitrogen immunodetection according to the manufacturer's protocol, and the enzyme concentration was expressed as ng/mL [55]. ELISA Assay for BAX content of MCF-7 cells was assessed by ELISA kit purchased from Cloud-Clone Crop. (USA) according to the manufacturer's protocol, and the enzyme concentration was expressed as ng/mL [56]. In Vitro Caspase-9 Activation Assay was performed using human active caspase-9 Invitrogen EIA kit and the procedure of the used kit was done according to the manufacturer's instructions [57].

Example 10. Colony Formation Assay

MCF-7 cells (600 cells per well) were seeded in 6-well plates and incubated for 24 h before being then treated with different doses of the compound 8c (50 and 250 nM) for 14 days. The cells were. Then the cells were washed with PBS twice and subsequently fixed with 4% paraformaldehyde and stained with 0.05% crystal violet for 30 min. Finally, cells were visualized using an inverted microscope.

Example 11. Wound Healing Assay

MCF-7 were grown in 6-well plates for 24 h, then the scratches were made using pipette tip and washed with PBS to remove non-adherent cell debris. Subsequently, the cells were treated with different concentrations of 8c for 24 h. The migrations across the wound area were photographed under a phase contrast microscopy.

Example 12. Measurement of Mitochondrial Depolarization Effect ($\Delta\psi_{mt}$) and ROS Levels in Cells Mitochondrial membrane potential ($\Delta\psi_{mt}$) was measured by flow cytometry with DiOC2(3) staining and additional labelling with an annexin V conjugate. After treatment with compound 8c (50 and 250 nM) and CA-4 (50 nM), cells were stained with DiOC2(3) dye for 30 min in the incubator then harvested and washed with PBS. DiOC2(3)-stained cells were resuspended with 1× annexin binding buffer then added annexin V conjugate and incubated at 37° C. for 15 min. Then the data obtained from flow cytometry were analyzed by Cell Quest software. Production of intracellular Reactive oxygen species (ROS) was measured using 2,7-dichlorofluorescin diacetate ($H_2$-DCFDA) dye. MCF-7 cells were seeded and treated either with vehicle (0.1% DMSO) or with compound 8c (50 and 250 nM) and CA-4 (50 nM) for different time 6, 12 and 24 h. $H_2O_2$ was used as a positive control. The amount of ROS generated was estimated after 2 h of selected compound treatment. The cells were collected by centrifugation and washed twice with PBS. Cells were then incubated with DCFDA dye (25 µM) in dark at 37° C. for 1 h. Fluorescence spectra (510-600 nm) were monitored using an excitation wavelength of 488 nm [58, 59]

Acknowledgement:

This project was funded by the Deanship of Scientific Research (DSR), at King Abdulaziz University, Jeddah, under grant no. (RG-18-166-41). The authors, therefore, acknowledge with thanks DSR for technical and financial support.

REFERENCES

1. Akhtar, M. J., et al., *Targeted anticancer therapy: overexpressed receptors and nanotechnology*. Clinica chimica acta, 2014. 436: p. 78-92.
2. Decosterd, L. A., et al., *Therapeutic drug monitoring of targeted anticancer therapy*. Biomarkers in medicine, 2015. 9(9): p. 887-893.
3. Lu, Y., et al., *An overview of tubulin inhibitors that interact with the colchicine binding site*. Pharmaceutical research, 2012. 29(11): p. 2943-2971.
4. Downing, K. H. and E. Nogales, *Tubulin and microtubule structure*. Current opinion in cell biology, 1998. 10(1): p. 16-22.
5. Pellegrini, F. and D. R. Budman, *Tubulin function, action of antitubulin drugs, and new drug development*. Cancer investigation, 2005. 23(3): p. 264-273.
6. Kavallaris, M., *Microtubules and resistance to tubulin-binding agents*. Nature Reviews Cancer, 2010. 10(3): p. 194-204.
7. Xu, Y.-R., et al., *Novel dibenzoxanthenes compounds inhibit human gastric cancer SGC-7901 cell growth by apoptosis*. Journal of Molecular Structure, 2020: p. 128588.
8. Perez, E. A., *Microtubule inhibitors: Differentiating tubulin-inhibiting agents based on mechanisms of action, clinical activity, and resistance*. Molecular cancer therapeutics, 2009. 8(8): p. 2086-2095.
9. Dumontet, C. and M. A. Jordan, *Microtubule-binding agents: a dynamic field of cancer therapeutics*. Nature reviews Drug discovery, 2010. 9(10): p. 790-803.
10. Sharma, S., et al., *Chalcone based azacarboline analogues as novel antitubulin agents: Design, synthesis, biological evaluation and molecular modelling studies*. European journal of medicinal chemistry, 2014. 85: p. 648-660.
11. Vilanova, C., et al., *Design and synthesis of pironetin analogue/combretastatin A-4 hybrids containing a 1, 2,*

3-*triazole ring and evaluation of their cytotoxic activity*. European journal of medicinal chemistry, 2014. 87: p. 125-130.
12. Kamal, A., et al., *Design and synthesis of pyrazole-oxindole conjugates targeting tubulin polymerization as new anticancer agents*. European journal of medicinal chemistry, 2015. 92: p. 501-513.
13. Jordan, A., et al., *Tubulin as a target for anticancer drugs: agents which interact with the mitotic spindle*. Medicinal research reviews, 1998. 18(4): p. 259-296.
14. Kaur, R., et al., *Recent developments in tubulin polymerization inhibitors: an overview*. European journal of medicinal chemistry, 2014. 87: p. 89-124.
15. Liu, Y.-M., et al., *Tubulin inhibitors: a patent review*. Expert opinion on therapeutic patents, 2014. 24(1): p. 69-88.
16. Buey, R. M., et al., *Microtubule interactions with chemically diverse stabilizing agents: thermodynamics of binding to the paclitaxel site predicts cytotoxicity*. Chemistry & biology, 2005. 12(12): p. 1269-1279.
17. Cragg, G. M., D. G. Kingston, and D. J. Newman, *Anticancer agents from natural products*. 2011: CRC press.
18. Fojo, T. and M. Menefee, *Mechanisms of multidrug resistance: the potential role of microtubule-stabilizing agents*. Annals of Oncology, 2007. 18(suppl_5): p. v3-v8.
19. Eckford, P. D. and F. J. Sharom, *ABC efflux pump-based resistance to chemotherapy drugs*. Chemical reviews, 2009. 109(7): p. 2989-3011.
20. Zweifel, M., et al., *Phase II trial of combretastatin A4 phosphate, carboplatin, and paclitaxel in patients with platinum-resistant ovarian cancer*. Annals of oncology, 2011. 22(9): p. 2036-2041.
21. Kamath, P. R., D. Sunil, and A. A. Ajees, *Synthesis of indole-quinoline-oxadiazoles: their anticancer potential and computational tubulin binding studies*. Research on Chemical Intermediates, 2016. 42(6): p. 5899-5914.
22. Khelifi, I., et al., *Design, synthesis and anticancer properties of IsoCombretaQuinolines as potent tubulin assembly inhibitors*. European journal of medicinal chemistry, 2017. 127: p. 1025-1034.
23. Nam, N.-H., *Combretastatin A-4 analogues as antimitotic antitumor agents*. Current medicinal chemistry, 2003. 10(17): p. 1697-1722.
24. Seligmann, J. and C. Twelves, *Tubulin: an example of targeted chemotherapy*. Future medicinal chemistry, 2013. 5(3): p. 339-352.
25. Pettit, G., et al., *Isolation and structure of the strong cell growth and tubulin inhibitor combretastatin A-4*. Experientia, 1989. 45(2): p. 209-211.
26. Das, B. C., et al., *Design and synthesis of 3, 5-disubstituted boron-containing 1, 2, 4-oxadiazoles as potential combretastatin A-4 (CA-4) analogs*. Tetrahedron letters, 2012. 53(31): p. 3947-3950.
27. Kaffy, J., et al., *1, 3-Dipolar cycloaddition route to novel isoxazole-type derivatives related to combretastatin A-4*. Tetrahedron letters, 2004. 45(17): p. 3359-3362.
28. Mahal, K., et al., *Combretastatin A-4 derived 5-(1-methyl-4-phenyl-imidazol-5-yl) indoles with superior cytotoxic and anti-vascular effects on chemoresistant cancer cells and tumors*. European journal of medicinal chemistry, 2016. 118: p. 9-20.
29. Perez-Melero, C., et al., *A new family of quinoline and quinoxaline analogues of combretastatins*. Bioorganic & medicinal chemistry letters, 2004. 14(14): p. 3771-3774.
30. Medarde, M., A. B. Maya, and C. Pérez-Melero, *Naphthalene combretastatin analogues: synthesis, cytotoxicity and antitubulin activity*. Journal of enzyme inhibition and medicinal chemistry, 2004. 19(6): p. 521-540.
31. Akhavan-Tafti, H., et al., *Characterization of acridan-carboxylic acid derivatives as chemiluminescent peroxidase substrates*. The Journal of Organic Chemistry, 1998. 63(4): p. 930-937.
32. Ibrahim, T. S., et al., *Design, Synthesis and Biological Evaluation of Novel 5-((substituted quinolin-3-yl/1-naphthyl) methylene)-3-substituted imidazolidin-2, 4-dione as HIV-1 Fusion Inhibitors*. Bioorganic Chemistry, 2020: p. 103782.
33. Zhou, Y., et al., *Design, synthesis and biological evaluation of 4-anilinoquinoline derivatives as novel potent tubulin depolymerization agents*. European journal of medicinal chemistry, 2017. 138: p. 1114-1125.
34. Hadfield, J. A., et al., *Tubulin and microtubules as targets for anticancer drugs*. Progress in Cell Cycle Research., 2003. 5: p. 309-326.
35. Ansari, M., et al., *New thiazole-2 (3H)-thiones containing 4-(3, 4, 5-trimethoxyphenyl) moiety as anticancer agents*. European journal of medicinal chemistry, 2020. 185: p. 111784.
36. Greene, L. M., M. J. Meegan, and D. M. Zisterer, *Combretastatins: more than just vascular targeting agents?* Journal of Pharmacology and Experimental Therapeutics, 2015. 355(2): p. 212-227.
37. Agut, R., et al., *Synthesis of Combretastatin A-4 and 3′-Aminocombretastatin A-4 derivatives with Aminoacid Containing Pendants and Study of their Interaction with Tubulin and as Downregulators of the VEGF, hTERT and c-Myc Gene Expression*. Molecules, 2020. 25(3): p. 660.
38. Pérez-Pérez, M.-J.s., et al., *Blocking blood flow to solid tumors by destabilizing tubulin: an approach to targeting tumor growth*. Journal of medicinal chemistry, 2016. 59(19): p. 8685-8711.
39. Mirzaei, S., et al., *Synthesis, structure-activity relationship and molecular docking studies of novel quinoline-chalcone hybrids as potential anticancer agents and tubulin inhibitors*. Journal of Molecular Structure, 2020. 1202: p. 127310.
40. Chaudhary, V., et al., *Novel combretastatin-2-aminoimidazole analogues as potent tubulin assembly inhibitors: exploration of unique pharmacophoric impact of bridging skeleton and aryl moiety*. Journal of medicinal chemistry, 2016. 59(7): p. 3439-3451.
41. Shobeiri, N., et al., *Synthesis and biological evaluation of quinoline analogues of flavones as potential anticancer agents and tubulin polymerization inhibitors*. European journal of medicinal chemistry, 2016. 114: p. 14-23.
42. Li, W., et al., *Discovery of novel quinoline-chalcone derivatives as potent antitumor agents with microtubule polymerization inhibitory activity*. Journal of medicinal chemistry, 2018. 62(2): p. 993-1013.
43. Mendez, G., et al., *Role of Bim in apoptosis induced in H460 lung tumor cells by the spindle poison Combretastatin-A4*. Apoptosis, 2011. 16(9): p. 940-949.
44. Tarade, D., et al., *Structurally simplified biphenyl combretastatin A4 derivatives retain in vitro anti-cancer activity dependent on mitotic arrest*. PloS one, 2017. 12(3).
45. Naaz, F., et al., *Design and synthesis of newer 1,3,4-oxadiazole and 1,2,4-triazole based Topsentin analogues as anti-proliferative agent targeting tubulin*. Bioorganic Chemistry, 2020. 95: p. 103519.
46. Hua, S., et al., *Dual-functional conjugates improving cancer immunochemotherapy by inhibiting tubulin* polymerization and indoleamine-2,3-dioxygenase. European Journal of Medicinal Chemistry, 2020. 189: p. 112041.
47. Bortolozzi, R., et al., *Evaluating the effects of fluorine on biological properties and metabolic stability of some antitubulin 3-substituted 7-phenyl-pyrroloquinolinones*. European journal of medicinal chemistry, 2019. 178: p. 297-314.
48. Xiong, S., et al., *Mitochondria-mediated apoptosis in mammals*. Protein & cell, 2014. 5(10): p. 737-749.
49. Zamzami, N., et al., *Sequential reduction of mitochondrial transmembrane potential and generation of reactive oxygen species in early programmed cell death*. The Journal of experimental medicine, 1995. 182(2): p. 367-377.
50. Romagnoli, R., et al., *Synthesis and biological evaluation of 2-methyl-4, 5-disubstituted oxazoles as a novel class of highly potent antitubulin agents*. Scientific reports, 2017. 7: p. 46356.
51. Romagnoli, R., et al., *Design and synthesis of potent in vitro and in vivo anticancer agents based on 1-(3', 4', 5'-trimethoxyphenyl)-2-aryl-1 H-imidazole*. Scientific reports, 2016. 6: p. 26602.
52. Hua, S., et al., *Dual-functional conjugates improving cancer immunochemotherapy by inhibiting tubulin polymerization and indoleamine-2, 3-dioxygenase*. European Journal of Medicinal Chemistry, 2020: p. 112041.
53. Wienecke, A. and G. Bacher, *Indibulin, a novel microtubule inhibitor, discriminates between mature neuronal and nonneuronal tubulin*. Cancer research, 2009. 69(1): p. 171-177.
54. Tahir, S. K., et al., *Rapid colchicine competition-binding scintillation proximity assay using biotin-labeled tubulin*. Biotechniques, 2000. 29(1): p. 156-160.
55. assets.thermofisher.com/TFS-Assets/LSG/manuals/ MAN0016621_244-3_HuBcl-2ELISA_UG.pdf.
56. abcam.com/ps/products/199/ab199080/documents/ ab199080_Human%20Bax%20Booklet_20200107%20 (website).pdf.
57. assets.thermofisher.com/TFS-Assets/LSG/manuals/ MAN0016485_2025_HuCaspase9ELISA_UG.pdf
58. Wu, D. and P. Yotnda, *Production and detection of reactive oxygen species (ROS) in cancers*. J Vis Exp, 2011(57).
59. Hura, N., et al., *Combretastatin-inspired heterocycles as antitubulin anticancer agents*. ACS omega, 2018. 3(8): p. 9754-9769.

The invention claimed is:
1. A method for treating cancer comprising administering to a subject in need thereof a therapeutically effective amount of a compound selected from the group consisting of

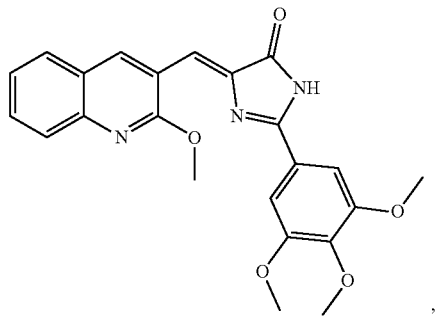

,

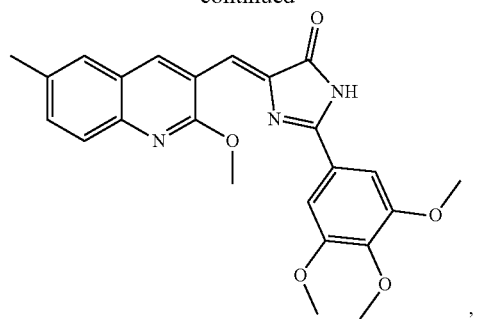

,

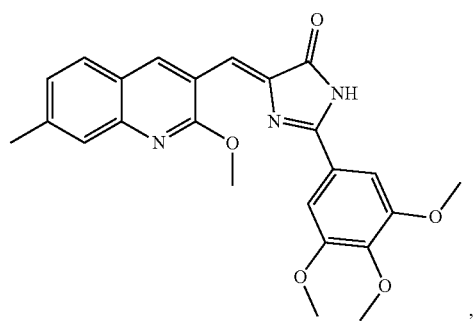

,

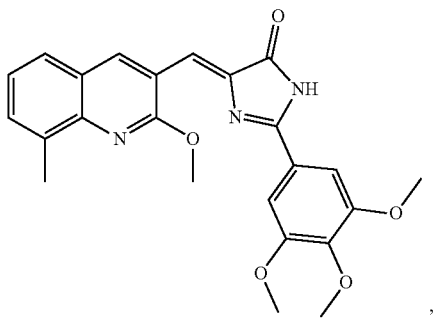

,

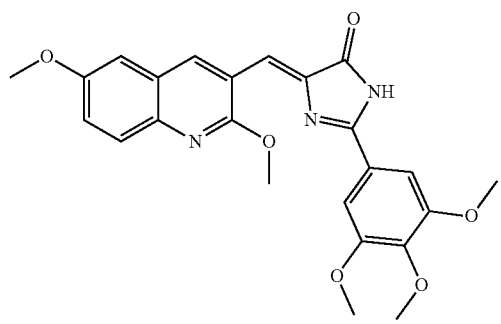

,

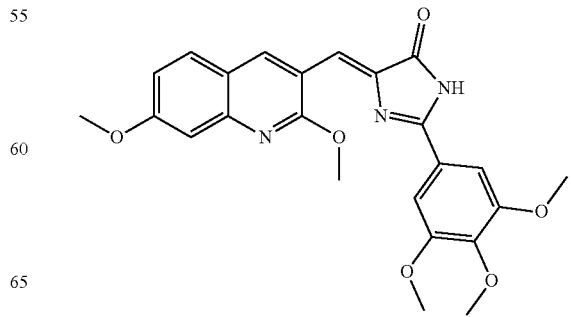

,

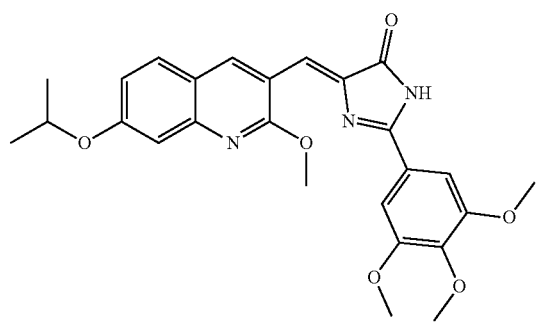

and

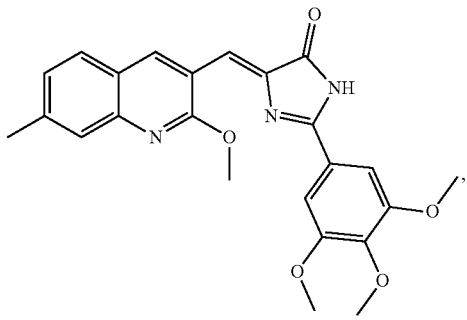

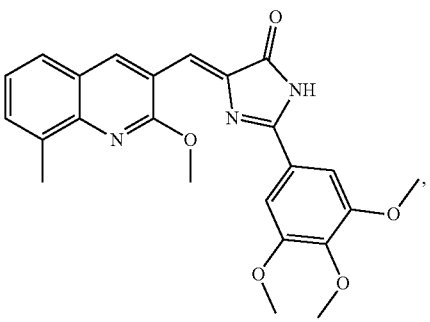

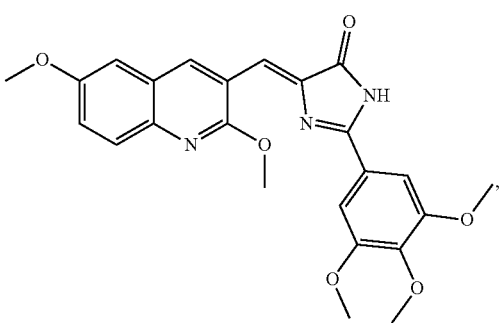

wherein the cancer is selected from the group consisting of breast cancer, colon cancer, cervical cancer or leukemia.

2. The method of claim 1, wherein the subject is mammalian.

3. The method of claim 1, wherein the subject is human.

4. A method of selectively killing or inhibiting the growth of a cancer comprising contacting the cancer cell with effective amount of a compound selected from the group consisting of

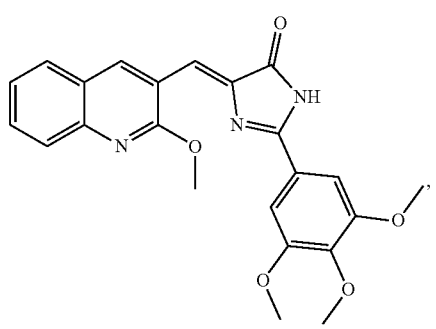

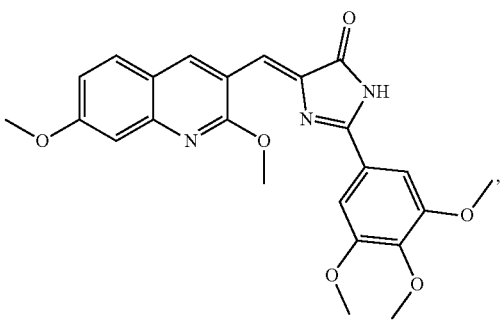

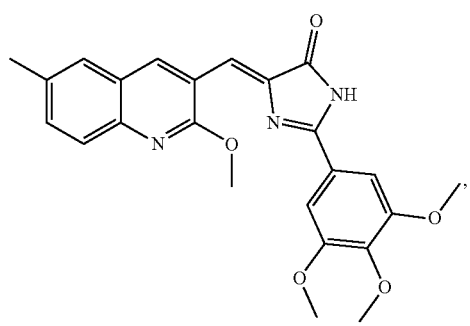

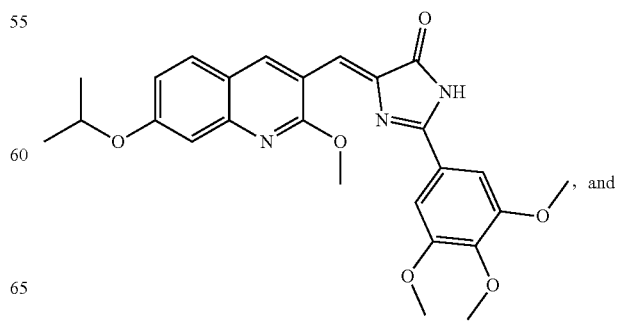

, and

-continued

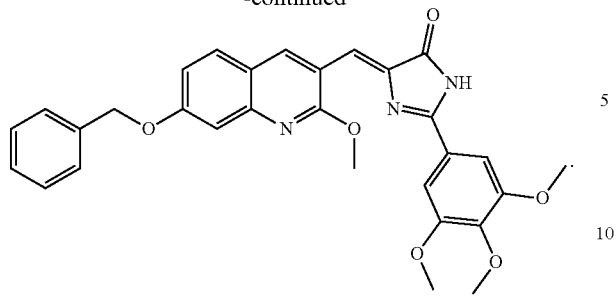

wherein the cancer is selected from the group consisting of breast cancer, colon cancer, cervical cancer or leukemia.

5. The method of claim 4, wherein the cancer cell is mammalian.

6. The method of claim 4, wherein the cancer cell is human.

7. The method of claim 4, wherein the cancer cell is in vitro.

8. The method of claim 4, wherein the cancer cell is in vivo.

9. The method of claim 4 wherein the compound is 4-[(2-Methoxy-7-methylquinolin-3-yl)methylene]-2-(3,4,5-trimethoxyphenyl)oxazol-5(4H)-one.

10. The method of claim 1 wherein the compound is 4-[(2-Methoxy-7-methylquinolin-3-yl)methylene]-2-(3,4,5-trimethoxyphenyl)oxazol-5(4H)-one.

* * * * *